(12) United States Patent
Charney et al.

(10) Patent No.: US 10,478,405 B2
(45) Date of Patent: *Nov. 19, 2019

(54) METHOD FOR TREATING POST-TRAUMATIC STRESS DISORDER

(71) Applicant: ICAHN SCHOOL OF MEDICINE AT MOUNT SINAI, New York, NY (US)

(72) Inventors: Dennis S. Charney, Chappaqua, NY (US); Adriana Feder, New York, NY (US)

(73) Assignee: Icahn School of Medicine at Mount Sinai, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/974,576

(22) Filed: Dec. 18, 2015

(65) Prior Publication Data
US 2016/0101069 A1    Apr. 14, 2016

Related U.S. Application Data

(63) Continuation of application No. 14/783,686, filed as application No. PCT/US2014/033997 on Apr. 14, 2014, now abandoned.
(Continued)

(51) Int. Cl.
*A61K 31/135*    (2006.01)
*A61K 45/06*    (2006.01)
(Continued)

(52) U.S. Cl.
CPC .......... *A61K 31/135* (2013.01); *A61K 9/0019* (2013.01); *A61K 9/0043* (2013.01);
(Continued)

(58) Field of Classification Search
None
See application file for complete search history.

(56) References Cited

U.S. PATENT DOCUMENTS

| 5,543,434 A | 8/1996 | Weg |
| 2007/0287753 A1 | 12/2007 | Charney |

(Continued)

FOREIGN PATENT DOCUMENTS

| CN | 101247795 | 8/2008 |
| CN | 101466364 | 6/2009 |

(Continued)

OTHER PUBLICATIONS

<https://www.merckmanuals.com/professional/psychiatric-disorders/anxiety-and-stressor-related-disorders/posttraumatic-stress-disorder-(ptsd)>> visited Mar. 25, 2016.*

(Continued)

*Primary Examiner* — Karl J Puttlitz
(74) *Attorney, Agent, or Firm* — Fish & Richardson P.C.

(57) ABSTRACT

The present disclosure provides compositions containing ketamine and methods of using those compositions for the treatment of post-traumatic stress disorder. Also provided herein is a pharmaceutical composition that comprises esketamine and a pharmaceutically acceptable carrier, excipient or diluent, for use in treatment of PTSD. In some aspects, the pharmaceutical composition is for intranasal or intravenous administration. In some aspects, the pharmaceutical composition is for use in a method of treating PTSD in a subject. In some aspects, the pharmaceutical composition is for use in a method of treating major depressive disorder in a subject that is co-morbid with the PTSD.

34 Claims, 3 Drawing Sheets

Related U.S. Application Data

(60) Provisional application No. 61/811,681, filed on Apr. 12, 2013, provisional application No. 61/915,947, filed on Dec. 13, 2013.

(51) Int. Cl.

| | |
|---|---|
| *A61K 31/428* | (2006.01) |
| *A61K 31/445* | (2006.01) |
| *A61K 31/4525* | (2006.01) |
| *A61K 31/517* | (2006.01) |
| *A61K 31/53* | (2006.01) |
| *A61K 33/00* | (2006.01) |
| *A61K 9/00* | (2006.01) |

(52) U.S. Cl.
CPC .......... *A61K 31/428* (2013.01); *A61K 31/445* (2013.01); *A61K 31/4525* (2013.01); *A61K 31/517* (2013.01); *A61K 31/53* (2013.01); *A61K 33/00* (2013.01); *A61K 45/06* (2013.01)

(56) References Cited

U.S. PATENT DOCUMENTS

| | | | |
|---|---|---|---|
| 2008/0305077 A1 | 12/2008 | Frey et al. | |
| 2010/0298305 A1 | 10/2010 | Capehart | |
| 2013/0165425 A1 | 6/2013 | Gless | |
| 2013/0236573 A1* | 9/2013 | Singh | A61K 31/137 424/730 |
| 2014/0057988 A1 | 2/2014 | Weg | |
| 2014/0079740 A1* | 3/2014 | Salama | A61K 9/2054 424/400 |
| 2015/0057317 A1* | 2/2015 | McCarthy | C12Q 1/6883 514/357 |

FOREIGN PATENT DOCUMENTS

| | | |
|---|---|---|
| DE | 102007009888 | 9/2008 |
| JP | 2011/504163 | 2/2011 |
| WO | 2004/045601 | 6/2004 |
| WO | 2006/121560 | 11/2006 |
| WO | 2007111880 * | 10/2007 |
| WO | 2008118785 * | 10/2008 |
| WO | 2013/138322 | 9/2013 |
| WO | 2014/020155 | 2/2014 |

OTHER PUBLICATIONS

Price et al., Biol Psychiatry 2009;66:522-526.*
Quevedo et al., Biomarkers Med. (2009) 3(1), 5-8.*
Womble et al., "Effects of Ketamine on Major Depressive Disorder in a Patient With Posttraumatic Stress Disorder", AANA Journal _ Apr. 2013, vol. 81, No. 2.*
McGhee et al., "The Correlation Between Ketamine and Post-traumatic Stress Disorder in Burned Service Members", The Journal of Trauma Injury, Infection, and Critical Care, vol. 64, No. 2, February Supplement 2008, pp. 195-199.*
Charney, "Ketamine as a Rapid Treatment for Post-traumatic Stress Disorder (PTSD) (KetPTSD)", U.S. National Library of Medicine, ClinicalTrials.gov., 9 pages, last updated on Dec. 12, 2012; https://clinicaltrials.gov/ct2/show/NCT00749203?term=ptsd+and+ketamine&draw=3&rank=8.*
Chedekel et al., "Yale: 'Magic' Antidepressant May Hold Promise for PTSD" (2012) at url : http://articles.courant.com/2012-06-03/health/hc-yale-drug-research-20120601_1_ptsd-debilitating-anxiety-disorder-ketamine retrieved Jun. 5, 2018 from the internet (Year: 2012).*
International Search Report for PCT/US2014/033997 dated Aug. 27, 2014. 4 pages.
"Subanesthetic Ketamine: How It Alters Physiology and Behavior in Humans", Rowland, Aviation, Space, and Environmental Medicine, vol. 76, No. 7, Jul. 1, 2005. 7 pages.
"Efficacy of Intravenous Ketamine for Treatment of Chronic Post-traumatic Stress Disorder A Radomized Clinical Trial", Feder et al., JAMA Psychiatry, Jun. 1, 2014, vol. 71, Iss 6, pp. 681-688.
Mathew et al., "Ketamine for Treatment-Resistant Unipolar Depression", CNS Drugs, 26(3):189-204, Mar. 2012.
Murrough al. "Antidepressant efficacy of ketamine in treatment-resistant major depression: a two-site, randomized controlled trial," The American Journal of Psychiatry. Oct. 1, 2013;170(10):1134-1142.
Noppers et al., "Absence of long-term analgesic effect from a short-term S-ketamine infusion on fibromyalgia pain: A randomized, prospective, double blind, active placebo-controlled trial," Eur. J. of Pain., 2011.
Paskalis et al., "Oral Administration of the NMDA Receptor Antagonist S-Ketamine as Add-on Therapy of Depression: A Case Series," Pharmacopsychiatry, 2010, pp. 33-35, vol. 40.
Paul et al., "Comparison of racemic ketamine and S-ketamine in treatment-resistant major depression: report of two cases," World J. of Bio. Psych., 2009, pp. 241-244, vol. 10(3).
Zarate et al., "A double-blind, placebo-controlled study of memantine in the treatment of major depression," Am J Psychiatry, 163(1):153-155, Jan. 2006.
Greist, "Posttraumatic Stress Disorder (PTSD)," Merck Manuals, May 2014, retrieved on Mar. 25, 2016, available online<https://www.merckmanuals.com/professional/psychiatric-disorders/anxiety-and-stressor-related-disorders/posttraumatic-stressdisorder-(ptsd), 4 pages.
Womble, "Effects of Ketamine on Major Depressive Disorder in a Patient With Posttraumatic Stress Disorder", AANA Journal, Apr. 2013, vol. 81, No. 2, pp. 118-119.
Chedekel, "Yale: 'Magie' Antidepressant May Hold Promise for PTSD", Jun. 3, 2012, The Hartford Courant, http://articles.courant.com/2012-06-03/health/hc-yale-drug-research-20120601_1_ptsd-debilitating-anxiety-disorder-ketamine; downloaded on Jan. 17, 2017, 2 pages.
Extended European Search Report for EP14783146.5 dated Dec. 19, 2016. 7 pages.
Non-Final Office Action for U.S. Appl. No. 14/783,686 dated Dec. 12, 2016. 15 pages.
"A Dose Escalation Study of Intranasal Neuropeptide Y in Post Traumatic Stress Disorder (PTSD)" updated Dec. 11, 2012, ClinicalTrials.gov archive, Developed by the National Library of Medicine, 4 pages.
Bajor et al., "The Psychopharmacology Algorithm Project at the Harvard South Shore Program: An Update on Posttraumatic Stress Disorder," Harvard Review of Psychiatry Sep./Oct. 2011, 19(5):240-258, cited as "'The Psychopharmacology Algorithm Project at the Harvard South Shore Program: An Update on Posttraumatic Stress Disorder,' Journal of International Psychiatry, Wei Zhaoguo et al., vol. 40, Issue No. 1, pp. 49-53" in Office Action in corresponding Chinese Application No. 201480033664.6, dated Aug. 7, 2017, 26 total pages.
Charney, "Ketamine as a Rapid Treatment for Post-traumatic Stress Disorder (PTSD) (KetPTSD)", U.S. National Library of Medicine, ClinicalTrials.gov., 9 pages, last updated on Dec. 12, 2012; https://clinicaltrials.gov/ct2/show/NCT00749203?term=ptsd+and+ketamine&draw=3&rank=8.
Hara et al., "Recent findings on drug therapy of PTSD," Traumatic Stress, 4(1)65-67, 2006.
Carr et. al., "Safety and efficacy of intranasal ketamine for the treatment of breakthrough pain in patients with chronic pain: a randomized, double-blind, placebo-controlled, crossover study," Pain, 2004, 108: 17-27.
Office Action in Israeli Application No. 242007, dated Jun. 7, 2018, 7 pages (with English translation).
Schonenberg et al., "Effects of peritraumatic ketamine medication on early and sustained posttraumatic stress symptoms in moderately injured accident victims," Psychopharmacology, 2005, 182(3):420-5.
McGhee et al., "The Intraoperative Administration of Ketamine to Burned U.S. Service Members Does Not Increase the Incidence of Post-Traumatic Stress Disorder", Military Medicine, vol. 179, August,

(56) References Cited

OTHER PUBLICATIONS

Supplement 2014, pp. 41-46. Doanloaded from https://academic.oup.com/milmed/article-abstract/179/suppl_8/41/4210165 by guest on Nov. 11, 2018. 6 pages.
Schonenberg et al., "Ketamine aggravates symptoms of acute stress disorder in a naturalistic sample of accident victims," J Psychopharmacol, Jul. 2008, 22: 493-7.

* cited by examiner

METHOD FOR TREATING POST-TRAUMATIC STRESS DISORDER

RELATED APPLICATIONS

This application is a continuation of U.S. patent application Ser. No. 14/783,686, filed Oct. 9, 2015 which is the U.S. National Phase Application under 35 U.S.C. § 371 of International Patent Application No. PCT/US2014/033997 filed Apr. 14, 2014, which claims priority to U.S. Provisional Application Ser. No. 61/811,681, filed Apr. 12, 2013, and 61/915,947, filed Dec. 13, 2013, both of which are incorporated by reference herein.

REFERENCE TO GOVERNMENT SUPPORT

This invention was made with government support under grant W81XWH-08-1-0602, awarded by the Department of the Army-USAMRAA. The U.S. government has certain rights in the invention.

TECHNICAL FIELD

This disclosure relates to the methods and compositions for treatment of post-traumatic stress disorder.

BACKGROUND

Post-traumatic stress disorder (PTSD) is a prevalent and highly debilitating psychiatric disorder that is notoriously difficult to treat. PTSD is characterized by flashbacks, emotional numbness, and insomnia, and is associated with functional impairments, physical health concerns, and mental health comorbidities, such as depression, with six fold higher risk of suicide. PTSD can result from a catastrophic and threatening event, e.g., a natural disaster, wartime situation, accident, domestic abuse, or violent crime. Symptoms typically develop within three months, but can emerge years after the initial trauma. At some point in their lifetimes, 5-8% of men and 10-14% of women, generally.

The treatment of PTSD is extremely challenging, and may include many years of individual and group therapy and medications such as antidepressants, anxiolytic drugs, β-adrenergic antagonists, opiates, or cortisol with variable results. Selective serotonin reuptake inhibitors (SSRIs) are currently recommended as the first-line pharmacotherapy. However, up to 40% of SSRI-treated PTSD patients do not respond and >70% never achieve full remission. The two SSRIs that are approved for PTSD by the United States Food and Drug Administration (FDA), paroxetine and sertraline, have modest effect sizes and limited efficacy in all three clusters of illness: re-experiencing, avoidance and numbing, and hyperarousal.

PTSD is particularly prevalent among combat veterans. An estimated 17% of Operation Iraqi Freedom/Operation Enduring Freedom veterans will develop PTSD. A recent Veterans Affairs (VA) clinical trial of the FDA-approved drug, sertraline, failed to show efficacy in a group of patients with predominantly combat-related PTSD. The severity and significance of lack of SSRI efficacy, especially in light of the observed relationship between trauma exposure and increased rates of disability, unemployment, and social assistance highlights the urgent need for novel pharmacological interventions targeting the core pathophysiology of PTSD.

Ketamine is an antagonist of NMDA-type glutamate receptors. Ketamine exhibits anesthetic properties at high doses, e.g., doses of ~2 mg/kg, and analgesic properties at subanesthetic doses. Ketamine is considered safe with minimal to moderate side effects.

There is a need in the art for improved methods for the treatment of PTSD. The present disclosure describes compositions and methods of using ketamine to treat PTSD.

SUMMARY

The present disclosure provides therapeutic agents and methods for treating PTSD.

In certain aspects, a method of treating post-traumatic stress disorder (PTSD) as provided herein includes treating a human individual suffering from PTSD with a therapeutically effective amount of ketamine. In some aspects, the effective amount of ketamine is a dose of about 0.01 to about 2.0 mg of ketamine per kilogram of body weight of the patient (mg/kg) to treat PTSD. In some aspects, the dose is about 0.05 to about 0.5 mg/kg of ketamine. In some aspects, the dose is less than about 0.5 mg/kg, less that about 0.4 mg/kg or less than about 0.3 mg/kg of ketamine. In some aspects, the effective amount of ketamine is a dose in the range of from about 0.01 mg/kg to about 2.0 mg/kg. In some aspects, the effective amount of ketamine is a dose in the range of from about 0.01 mg/kg to about 1.5 mg/kg. In some aspects, the effective amount of ketamine is a dose in the range of from about 0.01 mg/kg to about 1 mg/kg. In some aspects, the effective amount of ketamine is a dose in the range of from about 0.01 mg/kg to about 0.75 mg/kg. In some aspects, the effective amount of ketamine is a dose in the range of from about 0.75 mg/kg to about 1.5 mg/kg. In some aspects, the effective amount of ketamine is a dose in the range of from about 0.5 mg/kg to about 1.2 mg/kg. In some aspects, the effective amount of ketamine is a dose in the range of from about 0.05 mg/kg to about 0.5 mg/kg. In some aspects, the effective amount of ketamine is a dose of about 0.2 mg/kg or in an amount of about 0.4 mg/kg.

In some aspects, the total dose of ketamine is about 25 mg. In some aspects, the total dose of ketamine is about 50 mg. In some aspects, the total dose of ketamine is about 75 mg. In some aspects, the total dose of ketamine is about 100 mg. In some aspects, the total dose of ketamine is about 1.1 mg/kg. In some aspects, the total dose of ketamine is about 1.2 mg/kg 1.3 mg/kg, 1.4 mg/kg, 1.5 mg/kg, 1.6 mg/kg, 1.7 mg/kg, 1.8 mg/kg, 1.9 mg/kg, or 2.0 mg/kg.

In some aspects, the therapeutically effective amount of ketamine is a sub-anesthetic amount of ketamine for the individual. In some aspects, the therapeutically effective amount of ketamine is a sub-analgesic amount of ketamine for the individual. In some aspects, the individual is treated with ketamine via intravenous or intranasal administration. In some aspects, the individual is treated intranasally with ketamine, substantially only via the nasal respiratory epithelium, compared to treatment via the nasal olfactory epithelium. In some aspects, the individual is treated intranasally with ketamine, substantially only via the nasal olfactory epithelium, compared to treatment via the nasal respiratory epithelium. In some aspects, the individual is treated with a single dose of the therapeutically effective amount of ketamine. In some aspects, the individual is treated with multiple doses of the therapeutically effective amount of ketamine. In some aspects, the individual is treated with at least one dose of the therapeutically effective amount of ketamine per week for a period of two or more weeks.

In some aspects, the above methods for treating a human individual suffering from PTSD further include administering a second agent to treat the PTSD. In some aspects, the second active agent is an anti-depressant. In some aspects, the second active agent is paroxetine, sertraline, lithium, riluzole, prazosin, lamotrigine, or ifenprodil. In some aspects, the second agent is used as adjunctive therapy to ketamine treatment. In some aspects, the treatment includes a phase wherein treatment with the second agent takes place after treatment with ketamine as ceased. In some aspects, the treatment includes a phase where treatment with ketamine and treatment with the second agent overlap.

Also provided herein is a method of dosing treatment of PTSD with ketamine. The method can include treating an individual suffering from PTSD with one or more doses comprising a first amount of ketamine to treat PTSD and thereafter treating the individual with one or more doses comprising a second amount of ketamine to maintain treatment of the PTSD, where the second amount of ketamine is lower than the first amount of ketamine. In some aspects, the second amount of ketamine is an amount that is at most one-half, one-quarter, or one-tenth the amount of the first amount of ketamine. In some aspects, the method further includes treating major depressive disorder that is co-morbid with the PTSD. In some aspects, the ketamine is administered in a composition comprising a pharmaceutically acceptable carrier, excipient or diluent.

Also provided herein is a pharmaceutical composition that comprises ketamine and a pharmaceutically acceptable carrier, excipient or diluent, for use in treatment of PTSD. In some aspects, the pharmaceutical composition is for intra-nasal or intravenous administration. In some aspects, the pharmaceutical composition is for use in a method of treating PTSD in a subject. In some aspects, the pharmaceutical composition is for use in a method of treating major depressive disorder in a subject that is co-morbid with the PTSD.

In any of the above aspects, the ketamine can be esketamine. Thus, also provided is a method of treating PTSD comprising administering to a patient in need of such treatment an effective amount for treating PTSD of ketamine or esketamine.

Also provided herein is a method of treating PTSD that includes treating a human individual suffering from PTSD with a therapeutically effective amount of esketamine. In some aspects, the esketamine is administered in an amount in the range of from about 0.01 mg/kg to about 2.0 mg/kg. In some aspects, the esketamine is administered in an amount in the range of from about 0.01 mg/kg to about 1.5 mg/kg. In some aspects, the esketamine is administered in an amount in the range of from about 0.01 mg/kg to about 1 mg/kg. In some aspects, the esketamine is administered in an amount in the range of from about 0.01 mg/kg to about 0.75 mg/kg. In some aspects, the esketamine is administered in an amount in the range of from about 0.75 mg/kg to about 1.5 mg/kg. In some aspects, the esketamine is administered in an amount in the range of from about 0.5 mg/kg to about 1.2 mg/kg. In some aspects, the esketamine is administered in an amount in the range of from about 0.05 mg/kg to about 0.5 mg/kg. In some aspects, the esketamine is administered in an amount of about 0.2 mg/kg or in an amount of about 0.4 mg/kg.

In some aspects, the total dose of esketamine is about 25 mg. In some aspects, the total dose of esketamine is about 50 mg. In some aspects, the total dose of esketamine is about 75 mg. In some aspects, the total dose of esketamine is about 100 mg. In some aspects, the total dose of esketamine is about 1.1 mg/kg. In some aspects, the total dose of esketamine is about 1.2 mg/kg 1.3 mg/kg, 1.4 mg/kg, 1.5 mg/kg, 1.6 mg/kg, 1.7 mg/kg, 1.8 mg/kg, 1.9 mg/kg, or 2.0 mg/kg.

In some aspects, the esketamine is administered intravenously. In some aspects, the esketamine is administered intranasally. In some aspects, the method of treating PTSD further includes treating major depressive disorder that is co-morbid with the PTSD.

Also provided herein is a pharmaceutical composition that comprises esketamine and a pharmaceutically acceptable carrier, excipient or diluent, for use in treatment of PTSD. In some aspects, the pharmaceutical composition is for intra-nasal or intravenous administration. In some aspects, the pharmaceutical composition is for use in a method of treating PTSD in a subject. In some aspects, the pharmaceutical composition is for use in a method of treating major depressive disorder in a subject that is co-morbid with the PTSD.

DETAILED DESCRIPTION

Figure 1A:
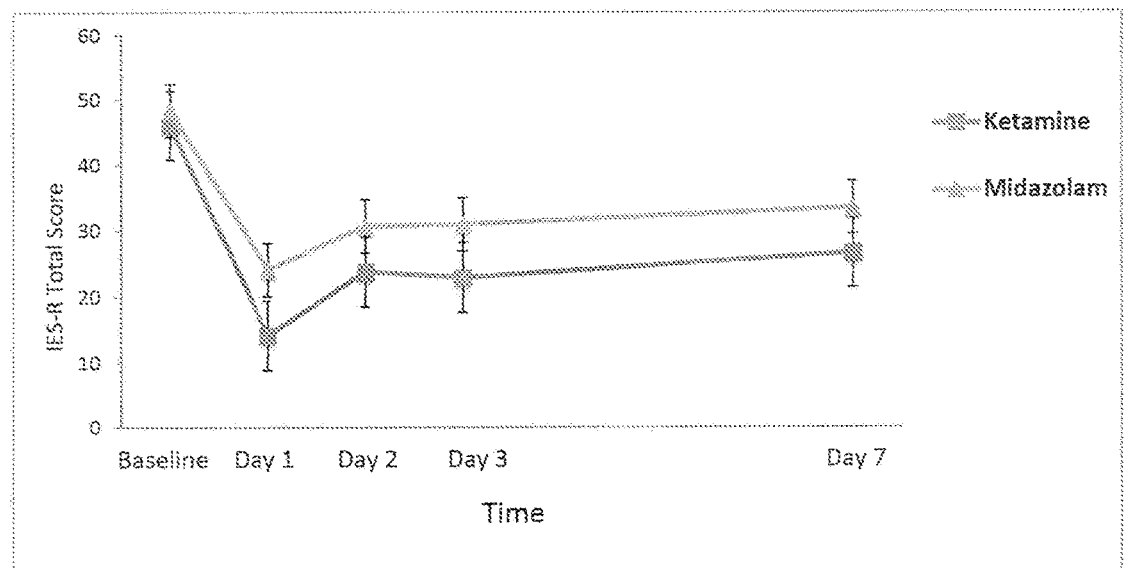
FIGS. 1A-1C contain graphs quantifying the change in the Impact of Event Scale-Revised (IES-R) total score (FIG. 1A), mean IES-R subscale score (FIG. 1B), and the Montgomery-Asberg Depression Rating Scale (MADRS) score over 1 week following the first infusion of ketamine or midazolam. Error bars indicate standard errors (n=41).

Key in the pathophysiology of PTSD is dysregulation of the stress response in response to traumatic events such as those encountered in chronic combat situations and extended deployment. The role of the human stress system is to respond to a stressor by activating not only the hypothalamic-pituitary-adrenocortical (HPA) axis, but also a complex cascade of reactions mediated by many other neurotransmitters, including excitatory and inhibitory amino acid neurotransmitters such as glutamate. While this response helps the species adapt and cope when the stressor is acute and short-lived, it may have pathological consequences when the stressor is chronic and overwhelming.

Preclinical studies have found that chronic stress is associated with extracellular glutamate accumulation, which results in sensitization of corticolimbic glutamatergic pathways and potentiation of the behavioral stress response. Persistent hyperactivity of this system may also contribute to glutamate-mediated excitotoxicity leading to hippocampal atrophy and, ultimately, memory disturbances, which are common in PTSD and other stress-related conditions such as major depression. Dysregulation of glutamatergic pathways has been hypothesized to play a central role in producing the core symptoms of PTSD, heightened stress sensitivity (startle), tension and anxiety, memory disturbances, and dissociation.

Recent evidence that conventional antidepressants have broad effects on specific glutamate receptors also suggests an approach to develop a novel class of drugs which may enhance neuronal plasticity and cellular resilience. Antagonists at the glutamatergic NMDA receptor may constitute such a novel class of drugs. Ketamine, a well-known FDA-approved analgesic and anesthetic medication which in glutamatergic pathways works as a high-affinity NMDA antagonist. An abundance of preclinical data suggests that ketamine also has antidepressant and anxiolytic properties.

As disclosed herein, ketamine is useful for the treatment of PTSD.

Definitions

The following definitions are provided for clarity and illustrative purposes only, and are not intended to limit the scope of the present disclosure.

The term "intranasal administration" in all its grammatical forms refers to administration of a drug through the nasal mucous membrane and through the nose-brain pathway directly into the cerebrospinal fluid.

The term "aerosol" refers to suspension in the air. In particular, aerosol refers to the particulization or atomization of a formulation disclosed herein and its suspension in the air. Thus, an aerosol formulation is a formulation comprising ketamine for intranasal administration.

Generally, "treating" or "treatment" of a state, disorder or condition includes: (1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disorder or a relapse thereof (in case of maintenance treatment) or at least one clinical or sub-clinical symptom thereof; or (3) relieving the disorder, i.e., causing regression of the state, disorder or condition or at least one of its clinical or sub-clinical symptoms. The benefit to a subject to be treated is either statistically significant or at least perceptible to the patient or to the physician.

The phrase "pharmaceutically acceptable" refers to molecular entities and compositions that are generally believed to be physiologically tolerable and do not typically produce an allergic or similar untoward reaction, such as gastric upset, dizziness and the like, when administered to a human. The term "pharmaceutically acceptable derivative" refers to any pharmaceutically acceptable salt, solvate or prodrug, e.g. ester, of a compound which upon administration to the recipient is capable of providing (directly or indirectly) a compound or an active metabolite or residue thereof. Such derivatives are recognizable to those skilled in the art, without undue experimentation. Derivatives are described, for example, in Burger's Medicinal Chemistry and Drug Discovery, 5th Edition, Vol 1: Principles and Practice, which is incorporated herein by reference to the extent of teaching such derivatives. Preferred pharmaceutically acceptable derivatives include salts, solvates, esters, carbamates, and phosphate esters. Particularly preferred pharmaceutically acceptable derivatives are salts, solvates, and esters. Most preferred pharmaceutically acceptable derivatives are salts and esters.

A "therapeutically effective amount" of a drug is an amount effective to demonstrate a desired activity of the drug. A therapeutically effective amount of ketamine is an amount effective to alleviate, i.e., noticeably reduce, one or more of the symptoms of a PTSD patient. A "therapeutically effective amount" will vary depending on the compound, the disorder and its severity and the age, weight, physical condition and responsiveness of the mammal to be treated.

The term "combination therapy" means the treatment of a subject in need of treatment with a certain composition or drug in which the subject is treated or given one or more other compositions or drugs for the disorder or condition in conjunction with the first and/or in conjunction with one or more other therapies, such as, e.g., a therapy such as a therapy comprising administering an anti-depressant agent. Combination therapy can be sequential therapy wherein the patient is treated first with one treatment modality (e.g., drug or therapy), and then the other (e.g., drug or therapy), and so on, or one more drugs and/or therapies can be administered simultaneously. In either case, these drugs and/or therapies are said to be "coadministered." It is to be understood that "coadministered" does not necessarily mean that the drugs and/or therapies are administered in a combined form (i.e., they may be administered separately or together to the same or different sites at the same or different times).

The details of one or more embodiments of the present disclosure are set forth in the description and claims below. The present disclosure is meant to be descriptive and illustrative and is not intended to limit the scope of the presently disclosed invention.

Overview

The present disclosure describes compositions and methods for the treatment of PTSD.

As described herein, ketamine can be used to effectively treat post-traumatic stress disorder (PTSD). Exemplary dosages of ketamine, e.g., intravenous and intranasal delivery of ketamine, are described below. Particularly preferred dosages of ketamine for the treatment of PTSD are subanesthetic doses of ketamine, e.g., a range from about 0.01 mg/kg to about 2.0 mg/kg, delivered, e.g., intranasally.

Ketamine ((2-(2-chlorophenyl)-2-(methylamino)-cyclohexanone) is a general anesthetic used by anesthesiologists, veterinarians, and researchers. Pharmacologically, ketamine is a noncompetitive NMDA receptor (NMDAR) antagonist. More specifically, ketamine binds to the allosteric site of the NMDA receptor, effectively inhibiting its channel. At high, fully anesthetic level doses, ketamine has also been found to bind to μ-opioid receptors type 2 in cultured human neuroblastoma cells—however, without agonist activity—and to sigma receptors in rats. Also, ketamine interacts with muscarinic receptors, descending monoaminergic pain pathways and voltage-gated calcium channels.

Ketamine is a chiral compound. The S(+) and R(−) stereoisomers bind NMDA receptors with different affinities: Ki=3200 and 1100 nM, respectively. Vranken et al. studied the use of an iontophoretic patch (a mechanism of delivery in which the electrically charged drug is transmitted by pulses of galvanic current) in 33 men and women in an investigation that studied the use of an iontophoretic patch to deliver ketamine for the treatment of intractable central neuropathic pain. S(+)-ketamine (also referred to as "(S)-ketamine" or "esketamine") was found to be two times more potent than racemic mixture of ketamine. Most pharmaceutical preparations of ketamine are racemic; however, some brands reportedly have (mostly undocumented) differences in enantiomeric proportions. The more active (S)-ketamine enantiomer is available for medical use under the brand name Ketanest S. Its hydrochloride salt is sold as Ketanest, Ketaset, and Ketalar. See, Paul et al., "Comparison of racemic ketamine and S-ketamine in treatment-resistant major depression: report of two cases", World J. of Bio. Psych., 2009, pp 241-244, Vol. 10(3) describe two cases studies in which patients with a history of recurrent major depression were treated with intravenous infusion of ketamine and S-ketamine; Paskalis et al., "Oral Administration of the NMDA Receptor Antagonist S-Ketamine as Add-on Therapy of Depression: A Case Series", Pharmacopsychiatry, 2010, pp 33-35, Vol. 40 present four case studies where depressed patients received 1.25 mg/kg oral S-ketamine as add-on to standard antidepressant therapy; Noppers et al., "Absence of long-term analgesic effect from a short-term S-ketamine infusion on fibromyalgia pain: A randomized, prospective, double blind, active placebo-controlled trial", Eur. J. of Pain., 2011, article in press, describe a trial assessing the analgesic efficacy of S-(+)-ketamine on fibromyalgia pain; Matthews et al., "Ketamine for Treatment-Resistant Unipolar Depression", CNS Drugs, 2012, pp 1-16, provide a review of emerging literature on ketamine and a review of the pharmacology of both ketamine and S-ketamine; and International Patent Publication No. WO2013138322. As used herein, "ketamine" includes preparations of ketamine that contain a racemic mixture of S(+) and R(−) stereoisomers of ketamine, preparations that contain differences in the enantiomeric proportions of the S(+) and R(−) stereoisomers, and preparations that contain only one of the enantiomers (e.g., only S(+) ketamine or only R(−) ketamine.

Intranasal administration of ketamine and midazolam to achieve sedation for ophthalmic surgery, and to induce anesthesia prior to elective surgery in healthy children has been reported. Ketamine has also been known to have analgesic properties; analgesia can be achieved with sub-anesthetic doses of ketamine. The drug is administered by various routes, including intravenous (i.v. or IV), intranasal (i.n. or IN), intramuscular (i.m. or IM), caudal, intrathecal, and subcutaneous (s.c.).

Subcutaneous administration of ketamine has been used to treat pain following surgery and associated with terminal cancer. Ketamine hydrochloride administered via a subcutaneous cannula was reported to successfully treat phantom limb pain.

Intravenous administration of ketamine has been used for the rapid treatment of treatment-resistant major depression. A 0.5 mg/kg intravenous infusion given over 40 minutes resulted in improvements in depression within 2 hours post-injection; and continued for up to 1 week. There were no serious adverse events. Zarate et al., Am J Psychiatry, 2006, 163:153-5. Intranasal (IN) ketamine plasma levels used for treatment of pain are 3-4 fold lower than the intravenous (IV) ketamine studies in depression. The slow infusion of ketamine produces gradually increasing plasma levels during the infusion period.

A typical ketamine dose for induction of anesthesia for surgical procedures is between 1.0-2.0 mg/kg, with additional ketamine used to sustain anesthesia. In anesthesia, the target ketamine blood level is reached with ketamine bolus doses between 0.2-0.26 mg/kg over 1 min. The dose for ketamine plasma levels to produce antidepressant responses as opposed to the levels needed to produce anesthesia is in the range of 0.5 mg/kg over 40 min. The reports of dissociation in pain studies were significantly lower than the IV studies in major depressive disorder because the ketamine levels achieved intranasally in these studies were much lower. The intranasal dose used for pain (50 mg) is roughly equivalent to 0.1 mg/kg i.v. of ketamine.

The present invention is directed to methods and compositions for treating PTSD using ketamine. Then present invention also encompasses methods and compositions for treating PTSD using esketamine. The treatments disclosed herein may be administered alone or may be supplemented with other antidepressant therapies, as described below.

Ketamine is an inexpensive, readily available drug, with minor adverse side effects. Thus, the invention contemplates additional savings to the overburdened health care system. Intranasal administration of this agent is rapid, allowing for fast action of the drug, and easily accomplished by a non-medically trained patient.

In some aspects, the PTSD-alleviating dose of ketamine is approximately 0.01 to approximately 3 mg/kg of body weight, approximately 0.01 to approximately 2 mg/kg of body weight, approximately 0.01 to approximately 1.5 mg/kg of body weight, approximately 0.05 to approximately 1.4 mg/kg of body weight, approximately 0.05 to approximately 1.3 mg/kg of body weight, approximately 0.05 to approximately 1.2 mg/kg of body weight, approximately 0.05 to approximately 1.1 mg/kg of body weight, approximately 0.01 to approximately 1 mg/kg of body weight, or approximately 0.05 to approximately 0.7 mg/kg of body weight.

In some aspects, the PTSD-alleviating dose of esketamine is approximately 0.01 to approximately 3 mg/kg of body weight, approximately 0.01 to approximately 2 mg/kg of body weight, approximately 0.01 to approximately 1.5 mg/kg of body weight, approximately 0.05 to approximately 1.4 mg/kg of body weight, approximately 0.05 to approximately 1.3 mg/kg of body weight, approximately 0.05 to approximately 1.2 mg/kg of body weight, approximately 0.05 to approximately 1.1 mg/kg of body weight, approximately 0.01 to approximately 1 mg/kg of body weight, or approximately 0.05 to approximately 0.7 mg/kg of body weight.

In some aspects, the PTSD-alleviating dose of ketamine is approximately 0.01 mg to about 1000 mg, or any amount or range therein, preferably from about 0.01 mg to about 500 mg, or any amount or range therein, preferably from about 0.1 mg to about 250 mg, or any amount or range therein. In another aspect, the PTSD-alleviating dose of ketamine is, e.g., 0.01 mg, 0.025 mg, 0.05 mg, 0.1 mg, 0.5 mg, 1 mg, 5 mg, 10 mg, 25 mg, 50 mg, 55 mg, 60 mg, 65 mg, 70 mg, 75 mg, 80 mg, 90 mg, 95 mg, 100 mg, 150 mg, 200 mg, 250 mg, or 500 mg.

In one aspect, the PTSD-alleviating dose of esketamine is approximately 0.01 mg to about 1000 mg, or any amount or range therein, preferably from about 0.01 mg to about 500 mg, or any amount or range therein, preferably from about 0.1 mg to about 250 mg, or any amount or range therein. In another aspect, the PTSD-alleviating dose of esketamine is, e.g., 0.01 mg, 0.025 mg, 0.05 mg, 0.1 mg, 0.5 mg, 1 mg, 5 mg, 10 mg, 25 mg, 50 mg, 55 mg, 60 mg, 65 mg, 70 mg, 75 mg, 80 mg, 90 mg, 95 mg, 100 mg, 150 mg, 200 mg, 250 mg, or 500 mg.

Ketamine has been used in the treatment of breakthrough pain (BTP) in chronic pain patients. In such patients, 10-50 mg of ketamine has been administered through intranasal administration in incremental 10 mg doses, every 90 seconds. The effect of that intranasal administration of ketamine was that there was a lower BTP in patients that received intranasal ketamine as opposed to placebo. There were very few side effects with such administration.

Formulations, Dosage Forms and Modes of Administration

While it is possible to use a composition disclosed herein (e.g., a composition comprising ketamine for therapy as is, it may be preferable to formulate the composition in a pharmaceutical formulation, e.g., in admixture with a suitable pharmaceutical excipient, diluent, or carrier selected with regard to the intended route of administration and standard pharmaceutical practice. Suitable carriers and their formulations are described in Remington: The Science and Practice of Pharmacy, 21$^{st}$ ed., 2005, Lippincott, Williams & Wilkins, Phila., Pa. Accordingly, in one aspect, a pharmaceutical composition or formulation comprises at least one active composition of ketamine in association with a pharmaceutically acceptable excipient, diluent, and/or carrier. The excipient, diluent and/or carrier must be "acceptable" in the sense of being compatible with the other ingredients of the formulation and not deleterious to the recipient thereof.

For in vivo administration to humans, the compositions can be formulated according to known methods used to prepare pharmaceutically useful compositions. Compositions may be designed to be short-acting, fast-releasing, long-acting, or sustained-releasing. Thus, pharmaceutical formulations may also be formulated for controlled release or for slow release.

When formulated in a pharmaceutical composition or formulation, ketamine can be admixed with a pharmaceutically acceptable carrier or excipient. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Other exemplary carriers include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like.

The compositions and formulations described herein may be for administration by oral (solid or liquid), parenteral (intramuscular, intraperitoneal, intravenous (IV) or subcutaneous injection), transdermal (either passively or using ionophoresis or electroporation), transmucosal (nasal, intranasal, vaginal, rectal, or sublingual), or inhalation routes of administration, or using bioerodible inserts and can be formulated in dosage forms appropriate for each route of administration. The most suitable route in any given case will depend on the particular host, and nature and severity of the conditions for which the active ingredient is being administered. The compositions may be conveniently presented in unit dosage form and prepared by any of the methods well known in the art of pharmacy, and using well known carriers and excipients.

In general, preparations according to this invention include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also optionally contain adjuvants, preserving, wetting, emulsifying, and dispersing agents. The pharmaceutical compositions may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Intravenous Administration

A preferred route of administration of ketamine is intravenous (IV). Ketamine may thus also be prepared in a formulation or pharmaceutical composition appropriate for IV administration. Ketamine can be admixed with a pharmaceutically acceptable carrier or excipient as described above. By way of example, ketamine can be formulated in a saline solution for intravenous administration.

Intranasal Administration

A preferred mode of administration is intranasal administration, i.e., through the nasal mucosa and through the nose-brain pathway directly into the cerebrospinal fluid. Ming Ming Wen, Discov Med, "Olfactory Targeting Through Intranasal Delivery of Biopharmaceutical Drugs to the Brain—Current Development," 2011, 11:497-503, is hereby incorporated by reference in its entirety. As discussed in Wen, drugs administered intranasally may reach the brain via alternatives pathways. In one pathway, drugs, e.g., ketamine, are absorbed systemically, following absorption through the blood vessels of the nasal respiratory epithelium. Drugs delivered via this systemic pathway must first cross the blood brain barrier, prior to reaching the brain. In an alternative delivery pathway, drugs administered intranasally can be rapidly transported into the CNS via the connection between the olfactory epithelium at the roof of the nasal cavity and the trigeminal system of the brain. This affords a direct connection, with no synapse between the olfactory neurons and the brain. The pathway thus allows transport of active agents to the brain without passage through the blood brain barrier.

Excipients that may improve intranasal administration of ketamine include mucoadhesives (e.g., carbopol, carboxymethylcellulose, and hyaluronan), penetration enhancers that improve permeability and bioavailability of ketamine upon contact of the nasal mucosa (e.g., peppermint oil, N-tridecyl-beta-D-maltoside, and hexarelin). Chitosan, for example, has both mucoadhesive and penetration enhancing properties. Other agents that can be used to in formulations for intranasal delivery include liposomes (e.g., cationic liposomes and liposomes coated with polyethylene glycol (PEG), vasoconstrictors (e.g., phenylephrine), to limit absorption through the systemic pathway and increase absorption through the olfactory epithelium. Additional formulations and methods for intranasal administration are found in Ilium, L., J Pharm Pharmacol, 56:3-17, 2004 and Ilium, L., Eur J Pharm Sci 11:1-18, 2000, each of which is hereby incorporated by reference in its entirety.

Either of liquid and powder intranasal formulations may be used. Ketamine, for example, may be combined with a dispersing agent, or dispersant, and administered intranasally in an aerosol formulation optimized for intranasal administration.

Intranasal liquid aerosol formulations contain ketamine and a dispersing agent in a physiologically acceptable diluent. Aerosolized formulations are broken down into liquid or solid particles in order to ensure that the aerosolized dose actually reaches the mucous membranes of the nasal passages. The term "aerosol particle" is used to describe the liquid or solid particle suitable for intranasal administration, i.e., that will reach the mucous membranes. Other considerations, such as construction of the delivery device, additional components in the formulation, and particle characteristics are important. These aspects of intranasal administration of a drug are well known in the art, and manipulation of formulations, aerosolization means and construction of a delivery device require at most routine experimentation by one of ordinary skill in the art.

Intranasal aerosol formulations can also be prepared as a dry powder formulation comprising a finely divided powder form of ketamine and a dispersant. For example, the dry powder formulation can comprise a finely divided dry powder containing ketamine, a dispersing agent and also a bulking agent. Bulking agents useful in conjunction with the present formulation include such agents as lactose, sorbitol, sucrose, or mannitol, in amounts that facilitate the dispersal of the powder from the device.

Nasal formulations may be administered with the aid of a delivery device, e.g., an aerosol delivery. Any form of aerosolization known in the art, including but not limited to spray bottles, nebulization, atomization or pump aerosolization of a liquid formulation, and aerosolization of a dry powder formulation, can be used.

Nasal formulations may be administered, for example, using a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation.

A useful device for intranasal administration is a small, hard bottle to which a metered dose sprayer is attached. In one embodiment, the metered dose is delivered by drawing the ketamine solution into a chamber of defined volume, which chamber has an aperture dimensioned to aerosolize and aerosol formulation by forming a spray when a liquid in the chamber is compressed. The chamber is compressed to administer the ketamine. In a specific embodiment, the chamber is a piston arrangement. Such devices are commercially available.

A preferred device for intranasal delivery of compositions and formulations is the OptiNose apparatus, which is commercially available from OptiNose US Inc. (Yardley, Pa.).

Other devices useful for administering a dose intranasally are mucosal automation device that provide atomization of topical solution across the nasal and oropharyngeal mucous membranes that produce a typical particle size of 30 microns. An example of such a device is the LMA MAD Nasal™ device (LMA Company, San Diego, Calif.), which produces a typical particle size of 30 microns, has a system dead space of 0.09 mL, a tip diameter of about 3/16" (4 mm), and an applicator length of about 1¾" (44 mm) can be used.

In another embodiment, intranasal drug delivery is achieved by taking a solubilized medication (liquid form) and dripping it into the nose a few drops at a time, allowing it to run down onto the nasal mucosa. This can be done using, e.g., a syringe.

In certain embodiments, the present disclosure provides liquid or powder aerosol formulations and dosage forms for intranasal administration (e.g., for use in treating subjects suffering from PTSD). In general such dosage forms contain ketamine in a pharmaceutically acceptable diluent. Pharmaceutically acceptable diluents in such liquid aerosol formulations include but are not limited to sterile water, saline, buffered saline, dextrose solution, and the like. In a specific embodiment, a diluent that may be used in the present disclosure and/or in a pharmaceutical formulation of the present disclosure is phosphate buffered saline or a buffered saline solution generally between the pH 7.0-8.0 range, or water. The present disclosure contemplates the use of any suitable diluent known in the art for intranasal administration.

Formulations may also include other agents, ingredients, and/or components, e.g., that are useful for pH maintenance, solution stabilization, or for the regulation of osmotic pressure, including, but not limited to salts, such as sodium chloride, or potassium chloride, and carbohydrates, such as glucose, galactose or mannose, and the like.

Formulations for intranasal administration may include a "mucosal penetration enhancer," i.e., a reagent that increases the rate or facility of transmucosal penetration of ketamine, such as but not limited to, a bile salt, fatty acid, surfactant or alcohol. Examples of penetration enhancers include sodium cholate, sodium dodecyl sulphate, sodium deoxycholate, taurodeoxycholate, sodium glycocholate, dimethylsulfoxide or ethanol.

Formulations disclosed herein, e.g., intranasal formulations, may include a dispersant. Preferably, a dispersant is pharmaceutically acceptable. Suitable dispersing agents are well known in the art, and include but are not limited to surfactants and the like. Such surfactants are generally used reduce surface induce aggregation caused by atomization of the solution forming a liquid aerosol. Examples of such surfactants include, but are not limited to, polyoxyethylene fatty acid esters and alcohols, and polyoxyethylene sorbitan fatty acid esters. Amounts of surfactants used will vary, being generally within the range or 0.001 and 4% by weight of the formulation. Suitable surfactants are well known in the art, and can be selected on the basis of desired properties, depending on the specific formulation.

Oral Administration

Contemplated for use herein are oral solid dosage forms, which are described generally in Remington's Pharmaceutical Sciences, 18th Ed. 1990 (Mack Publishing Co. Easton Pa. 18042) at Chapter 89). Solid dosage forms include tablets, capsules, pills, troches or lozenges, cachets, pellets, powders, or granules. An exemplary lozenge formulation is described in Chong et al. Clin Drug Investig. 2009; 29(5): 317-24. Also, liposomal or proteinoid encapsulation may be used to formulate the present compositions (as, for example, proteinoid microspheres reported in U.S. Pat. No. 4,925, 673). Liposomal encapsulation may be used and the liposomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979. In general, the formulation includes the therapeutic agent and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants, wetting agents, emulsifying and suspending agents; and sweetening, flavoring, coloring, and perfuming agents.

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine, e.g., by the use of an enteric coating. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used. The formulation of the material for capsule administration could also be as a powder, lightly compressed plugs, or even as tablets. These therapeutics could be prepared by compression.

One may dilute or increase the volume of the therapeutic agent with an inert material. These diluents could include carbohydrates, especially mannitol, lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic agent into a solid dosage form. Materials used as disintegrants include but are not limited to starch, including the commercial disintegrant based on starch, Explotab, Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders, and can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties drug during formulation and to aid rearrangement during compression might be added. The glidants may include starch, talc, pyrogenic silica and hydrated silicoaluminate.

To aid dissolution of the therapeutic agent into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Controlled release oral formulations may used in practicing the present invention. The therapeutic agent could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e., the therapeutic agent is enclosed in a semipermeable membrane which allows water to enter and push agent out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid. A mix of materials might be used to provide the optimum film coating. Film coating may be carried out in a pan coater or in a fluidized bed or by compression coating.

Transdermal Administration

In another alternative embodiment, administration comprises transdermal administration. Such treatment may be administered alone or may be supplemented with other antidepressant therapies as described herein. Transdermal administration includes passive or active transdermal or transcutaneous modalities, including, for example, patches and iontophoresis devices, as well as topical application of pastes, salves, or ointments.

Those of skill in the art are well aware of general technologies for transdermal drug delivery or administration of a therapeutic agent to the skin. Transdermal drug delivery offers controlled release of a drug to the patient and transdermal patches are user-friendly, convenient, painless, and offer multi-day dosing which usually results in improved patient compliance. The methods of the invention for treating PTSD patients with a transdermal administration of ketamine can include administering ketamine to skin of the face, head or body. Such a ketamine composition can be administered to the skin of the face, scalp, temporal region, arms, stomach, thighs, back, neck and the like. Suitable skin of the face includes skin of the chin, the upper lip, the lower lip, the forehead, the nose, the cheek, the skin around the eyes, the upper eyelid, the lower eyelid or combinations thereof. Suitable skin of the scalp includes the front of the scalp, the scalp over the temporal region, the lateral part of the scalp, or combinations thereof. Suitable skin of the temporal region includes the temple and the scalp over the temporal region and combinations thereof. The ketamine may be formulated into a bioadhesive patch or a bioadhesive strip with an occlusive covering. Alternatively, the transdermal ketamine composition for administration to the skin can be applied as a topical ointment, a topical gel, a lotion, a cream, a solution, a spray, a paint, a film, a foil, a cosmetic, to be applied to the skin in a layer with or without an occlusive dressing.

Intradermal administration of ketamine-containing compositions also is contemplated. Intradermal administration of a therapeutic agent is defined as within or between the layers of skin. In contrast, subcutaneous administration is defined as beneath the initial layer of skin and intravenous is a systemic administration into the bloodstream. Administration of therapeutic agents by intradermal, intravenous or subcutaneous injection is a common means of drug delivery and readily performed by one skilled in the art.

The compositions and formulation described herein may be administered by a health professional or by a patient. Patient self-administration of ketamine to treat PTSD is expressly contemplated. Intranasal administration and administration via transdermal patch are particularly suited to patient self-administration.

Additional Active Ingredients

Formulations for use in the methods described herein can include other therapeutically or pharmacologically active ingredients in addition to ketamine, such as but not limited to agents used for antidepressant therapy. Such agents include, but are not limited to, antidepressants: e.g., biogenic amine non-selective reuptake inhibitors, e.g., tricyclic antidepressants like imipramine; serotonin selective reuptake inhibitors like fluoxetine (Prozac); monoamine oxidase inhibitors (MAO-I) like phenelezine; other types of antidepressant medications including atypical antidepressants. Antidepressants augmentation with other medications e.g., lithium, T3, T4, etc. Other treatment modalities with antidepressant effects: electro-convulsive treatment (ECT); light therapy, psychotherapy e.g., cognitive or interpersonal therapy for PTSD.

In addition, administration of drugs, reported to ameliorate or exacerbate the symptoms of a neuropsychiatric disorder, include but are not limited to compounds include antidepressants such as lithium salts, carbamazepine, valproic acid, lysergic acid diethylamide (LSD), p-chlorophenylalanine, p-propyidopacetamide dithiocarbamate derivatives e.g., FLA 63; anti-anxiety drugs, e.g., diazepam; monoamine oxidase (MAO) inhibitors, e.g., iproniazid, clorgyline, phenelzine, tranylcypromine, and isocarboxazid; biogenic amine uptake blockers, e.g., tricyclic antidepressants such as desipramine, imipramine and amitriptyline; atypical antidepressants such as mirtazapine, nefazodone, bupropion; serotonin reuptake inhibitors e.g., fluoxetine, venlafaxine, and duloxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), S and dibenzodiazepines (e.g., clozapine); benzodiazepines; dopaminergic agonists and antagonists e.g., L-DOPA, cocaine, amphetamine, a-methyl-tyrosine, reserpine, tetrabenazine, benztropine, pargyline; noradrenergic agonists and antagonists e.g., clonidine, phenoxybenzamine, phentolamine, tropolone.

In another embodiment of the treatment methods, the compositions administered comprise compounds, in particular drugs, reported to ameliorate or exacerbate the symptoms of oxidative stress disorder. Such compounds include reduced IS glutathione (GSH), glutathione precursors, e.g., N-acetylcysteine; antioxidants, e.g., vitamins E and C, beta carotene and quinones; inhibitors of lipid membrane peroxidation, e.g., 21-aminosteroid U74006F (tirilazad mesylate), and lazaroids; antioxidants such as mazindol; 2c dizocilpine maleate; selegiline; sulfhydryls N-acetyleysteine and cysteamine; dimethylthiourea; EUK-8 a synthetic, low molecular salen-manganese complex; synthetic manganese-based metalloprotein superoxide dismutase mimic, SC52608; free radical scavengers or suppressors, e.g., pegorgotein, tocotrienol, tocopheral, MDL 74,18, LY231617, MCI-186, AVS (nicaraven), allopurinol, rifampicin, oxypurinol, hypochlorous acid or recombinant human Cu, Zn-SOD.

Dosages

Effective amounts of ketamine in compositions including pharmaceutical formulations, include doses that partially or completely achieve the desired therapeutic, prophylactic, and/or biological effect. In a specific embodiment, an effective amount of ketamine administered to a subject with PTSD is effective for treating one or more signs or symptoms of PTSD. The actual amount effective for a particular application depends on the condition being treated and the route of administration.

In certain aspect, the present disclosure provides for administration of a therapeutically effective dose of ketamine, i.e., a dose effective to treat PTSD. Specific dosages may be adjusted depending on conditions of disease, i.e., the severity of PTSD, the age, body weight, general health conditions, sex, and diet of the subject, dose intervals, administration routes, excretion rate, and combinations of drugs. Any of the dosage forms described herein containing effective amounts of ketamine, either alone or in combination with one or more active agents, are well within the bounds of routine experimentation and therefore, well within the scope of the instant invention.

An initial dose may be larger, followed by smaller maintenance doses. The dose may be administered as infrequently as weekly or biweekly, or fractionated into smaller doses and administered daily, several times daily, semi-weekly, bi-weekly, quarterly, etc., to maintain an effective dosage level. Preliminary doses can be determined according to animal tests, and the scaling of dosages for human administration can be performed according to art-accepted practices. In certain embodiments, a subject may be administered 1 dose, 2 doses, 3 doses, 4 doses, 5 doses, 6 doses or more of a ketamine-containing composition described herein. However, other ranges are possible, depending on the subject's response to the treatment. Moreover, an initial dose may be the same as, or lower or higher than subsequently administered doses of ketamine.

The number and frequency of doses may be determined based on the subject's response to administration of the composition, e.g., if one or more of the patient's symptoms improve and/or if the subject tolerates administration of the composition without adverse reaction; in some subjects, a single dose is sufficient, other subjects may receive a daily, several times a day, every other day, several times per week, weekly, biweekly, semi-weekly, or monthly administration of a composition containing ketamine as described herein. The duration and frequency of treatment will depend upon the subject's response to treatment, i.e., if the subject's condition and/or one more symptoms of PTSD improves.

In one example of a dosing regimen, an initial dose of ketamine is used to treat PTSD, followed by titration of to a lower dose of ketamine to maintain treatment of the PTSD. Such a regimen may be particularly useful, for example, to use a high dose of ketamine to treat acute symptoms of PTSD, followed by titrating to a lower dose of ketamine, to treat chronic symptoms of PTSD.

In some aspects, a dose of ketamine to treat PTSD is approximately 0.001 to approximately 2 mg/kg body, 0.01 to approximately 1 mg/kg of body weight, or approximately 0.05 to approximately 0.7 mg/kg of body weight. A subject (e.g., patient) suffering from PTSD may be administered (including self administration) a dose of ketamine of, for example, about 0.01 mg per kg of body weight (mg/kg), about 0.05 mg/kg, 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, or about 3 mg/kg.

In another embodiment, the total dose of ketamine per nasal administration ranges from about 1 to about 250 mg. By way of non-limiting example, ketamine doses of 1 mg, 2 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, and 250 mg are specifically contemplated.

In a certain embodiments, an intranasal or intravenous dose of ketamine for a subject of 80 kg body weight is equal to or greater than about 40 mg, for example, about 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, or 250 mg.

In certain embodiments, intranasal administration of 8-32 mg of ketamine, corresponding to 0.13 to 0.53 mg/kg of body weight is contemplated.

In some aspects, a dose of esketamine to treat PTSD is approximately 0.001 to approximately 2 mg/kg body, 0.01 to approximately 1 mg/kg of body weight, or approximately 0.05 to approximately 0.7 mg/kg of body weight. A subject (e.g., patient) suffering from PTSD may be administered (including self administration) a dose of esketamine of, for example, about 0.01 mg per kg of body weight (mg/kg), about 0.05 mg/kg, 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, or about 3 mg/kg.

In another embodiment, the total dose of esketamine per intranasal administration ranges from about 1 to about 250 mg. By way of non-limiting example, esketamine doses of 1 mg, 2 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, and 250 mg are specifically contemplated.

In another embodiment, the total dose of ketamine per intranasal administration ranges from about 10 mg to about 300 mg, about 10 mg to about 250 mg, about 10 to about 200 mg, about 15 to about 175 mg, about 20 to about 175 mg, about 25 to about 150 mg, about 25 to about 125 mg, about 25 to about 100 mg, about 50 to about 100 mg, about 50 mg to about 75 mg, about 75 mg to about 100 mg, or about 75 mg to about 200 mg.

In another embodiment, the total dose of esketamine per intranasal administration ranges from about 10 mg to about 300 mg, about 10 mg to about 250 mg, about 10 to about 200 mg, about 15 to about 175 mg, about 20 to about 175 mg, about 25 to about 150 mg, about 25 to about 125 mg, about 25 to about 100 mg, about 50 to about 100 mg, about 50 mg to about 75 mg, about 75 mg to about 100 mg, or about 75 mg to about 200 mg.

In a certain embodiments, an intranasal or intravenous dose of esketamine for a subject of about 70-80 kg body weight is equal to or greater than about 40 mg, for example, about 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, or 250 mg.

In certain embodiments, intranasal administration of 8-32 mg of esketamine, corresponding to 0.13 to 0.53 mg/kg of body weight is contemplated. In another embodiment, intranasal administration of a total dose of between about 50-75 mg of esketamine, corresponding to between about 0.83 to 1.25 mg/kg of body weight is contemplated. In another embodiment, intranasal administration of a total dose of between about 50-75 mg of esketamine, corresponding to between about 0.74 to 1.1 mg/kg of body weight is contemplated.

In certain embodiments, intranasal administration of 8-32 mg of ketamine, corresponding to 0.13 to 0.53 mg/kg of body weight is contemplated. In another embodiment, intranasal administration of a total dose of between about 50-75 mg of ketamine, corresponding to between about 0.83 to 1.25 mg/kg of body weight is contemplated. In another embodiment, intranasal administration of a total dose of between about 50-75 mg of ketamine, corresponding to between about 0.74 to 1.1 mg/kg of body weight is contemplated.

Preferably, the effective dose of ketamine is titrated under the supervision of a physician or medical care provider, so that the optimum dose for the particular application is accurately determined Thus, the present disclosure provides a dose suited to each individual subject (e.g., patient).

Once a dosage range is established, an advantage of compositions for intranasal administration of ketamine and methods of treatment via intranasal administration is that the patient can administer (e.g., self-administer) ketamine on an as-needed, dose-to-effect basis. Thus, the frequency of administration is under control of the subject. Yet another particular advantage is that intranasal administration of ketamine is non-invasive, and facilitates ketamine's crossing of the blood-brain barrier.

The mild adverse effects of ketamine, e.g., dysphoria and/or hallucinations, sometimes called "ketamine dreams," can occur upon administration of a dose of greater than 50 mg of ketamine, and usually require doses greater than 100 mg of ketamine of total dose intranasally. When administering ketamine to treat PTSD, it is preferable to administer a dose that is effective in treating PTSD, but is below the level that results in such side effects. It is possible, however, that higher doses of ketamine may be administered, particularly in response to an acute episode of PTSD. Thus, co-administration of a ketamine with the additional exemplary agents noted above may be indicated in order to achieve the beneficial anti-PTSD effects of ketamine without the side effects of this agent.

Methods of Treating Post-Traumatic Stress Disorder

Methods for treating a human patient with PTSD are directed to using ketamine to reduce or eliminate at least one symptom of PTSD in the patient. Ketamine may be administered as a racemic mixture of (S)-ketamine and (R)-ketamine, or as enantiomerically enriched for a ketamine enantiomer. A composition may be enriched to the extent that it is, for example, 90%, 95%, 99%, 99.9 or 99.99% of either of the (S)-ketamine and (R)-ketamine enantiomer.

In a specific embodiment, a method for treating a human patient with PTSD is directed to using esketamine to reduce or eliminate at least one symptom of PTSD in the patient.

In certain embodiments, a composition comprising ketamine is administered intranasally or intravenously to a patient suffering from PTSD. In some embodiments, one or more secondary active agents, such as one of those described above, are coadministered to a patient in a combination therapy. As discussed above, "coadministered" does not necessarily mean that the drugs and/or therapies are administered in a combined form (i.e., they may be administered separately (i.e., as separate compositions or formulations) or together (the same formulation or composition) to the same or different sites at the same or different times). In one embodiment, a patient suffering from PTSD is administered a combination therapy comprising ketamine and an antidepressant agent (e.g., SSRI).

In other embodiments, the present disclosure also contemplates the prophylactic use of the ketamine-containing compositions and formulations disclosed herein. For example, in certain embodiments, presently provided are methods for inhibiting development of post-traumatic stress disorder (PTSD) in a human patient which comprises intranasally or intravenously administering to a subject in need of such inhibiting a composition comprising a therapeutically effective amount of ketamine for inhibiting the development of PTSD and/or one the development of one or more PTSD-like symptoms, wherein the therapeutically effective amount is a dosage range of about dose of between about 0.1 mg/kg per day to about 3.0 mg/kg/day. Thus, in certain embodiments, for example, a subject may be administered (including self-administered) a composition or formulation comprising a therapeutically effective amount of ketamine prior to a situation in which the subject is likely to be exposed to traumatic stress, such as early responders or military personnel, immediately after exposure to traumatic stress, and/or when the subject feels that his or her PTSD symptoms are likely to appear.

In specific embodiments, the symptoms of PTSD are alleviated within 2 hours of administration of the ketamine. As disclosed herein, symptoms of PTSD may be alleviated concomitant with administration of ketamine.

Treatment of PTSD may be achieved administration of a single dose of the ketamine. Alternatively, multiple doses of ketamine may be administered. Administration of a single dose of ketamine can be sufficient to alleviate the effects of the PTSD for 7 days, 2 weeks and in some cases, longer.

IV administration of ketamine can be on an as needed basis, e.g., when symptoms of PTSD appear. For IV administration, ketamine (e.g., doses of at least 0.5 mg/kg) may be administered over a period of 40 minutes. IV administration may be continued for up to 1 week, or longer. IV administration of ketamine may also be effected at least twice, at least three times, at least four times, at least five time, at least six times, at least seven times per week, and may be continued over a period of two, three, four, five, six, seven, eight, nine or 10 weeks, or more. No serious adverse events caused by IV administration of ketamine have been observed. Any side effects observed are typically mild, e.g., euphoria, elevated BP, increased libido, perceptual disturbances, and furthermore these effects typically abate within 80 minutes post-infusion.

Administration of intranasal ketamine can be on an as needed basis, e.g., when symptoms of PTSD appear. In specific embodiments, the ketamine is administered at least two, at least three, at least four, at least five, at least six, at least seven, at least eight, at least nine times in fourteen days. In other embodiments, the ketamine is administered at least two, at least three, at least four, at least five, at least six, at least seven, at least eight, at least nine times in twenty-one days. In other embodiments, the intranasal ketamine is administered at least once a day, at least twice a day, at least three times per day, or more. In other embodiments, the intranasal ketamine is administered at least once a week, at least twice a week, at least three times per week, or more frequently. In another embodiment, the intranasal ketamine is administered at least twice per months, or at least once per months. Treatment can continue as long as needed.

Ketamine may also be used to treat PTSD in combination with a second agent. When used in combination with ketamine, a second agent may be administered as an adjunct therapy to ketamine, i.e., an individual suffering from PTSD may be treated concurrently with ketamine and the second agent. Alternatively, an individual suffering from PTSD may be treated initially with ketamine, followed by cessation of ketamine treatment and initiation of treatment with a second agent. Such a treatment may be warranted, for example, if a patient exhibits unwanted side effects or reduced response to ketamine treatment. Alternatively, in certain embodiments, ketamine is used as an initial treatment for PTSD, e.g., by administration of one, two or three doses, and a second agent is administered to prolong the effect of ketamine on reducing PTSD, or alternatively, to boost the effect of ketamine reducing PTSD. A person of ordinary skill in the art will recognize that other variations of the presented schemes are possible, e.g., initiating treatment of a PTSD patient with ketamine, followed by a period wherein the patient is treated with a second agent as adjunct therapy to ketamine treatment, followed by cessation of ketamine treatment.

Exemplary second agents for use with ketamine to treat PTSD are anxiolytics, antidepressants, including for example, SRIs, SSRI and lithium. Specific examples of second agents for use with ketamine in treating PTSD are paroxetine, sertraline, lithium, riluzole, prazosin, lamotrigine, and ifenprodil.

In certain embodiments, a second agent is used in combination with ketamine to treat PTSD, or following an initial treatment phase of PTSD with ketamine, wherein the second agent boosts the positive effect or ketamine in treatment of PTSD or sustains the positive effect of ketamine in treatment of PTSD.

In alternative embodiments, intravenous, oral, and transdermal administration of ketamine are contemplated. In one alternative embodiment, the invention thus provides a method of treating a human patient for PTSD, comprising intravenously administering a composition comprising ketamine to the patient at a dosage sufficient to reduce or eliminate the symptoms of the PTSD. In another alternative embodiment, the invention thus provides a method of treating a human patient for PTSD, comprising transdermally administering a composition comprising ketamine to the patient at a dosage sufficient to reduce or eliminate the symptoms of the PTSD. In another alternative embodiment, the invention thus provides a method of treating a human patient for PTSD, comprising orally (e.g., liquid or solid (e.g., lozenge) dosage form) administering a composition comprising ketamine to the patient at a dosage sufficient to reduce or eliminate the symptoms of the PTSD. In more specific embodiments, the ketamine is in a pharmaceutically acceptable carrier and is administered at a dose of between about 0.1 mg/kg per day to about 3.0 mg/kg/day.

The methods of the invention may be achieved through a method that comprises intravenous, oral, or transdermal administration of multiple doses of the ketamine. Administration intravenous, oral, or transdermal administration ketamine can be on an as needed basis, e.g., when symptoms of PTSD appear. In specific embodiments, the ketamine is administered at least two, at least three, at least four, at least five, at least six, at least seven, at least eight, at least nine times in fourteen days. In other embodiments, the ketamine is administered at least two, at least three, at least four, at least five, at least six, at least seven, at least eight, at least nine times in twenty-one days. In other embodiments, the ketamine is administered at least once a day, at least twice a day, at least three times per day, or more. In other embodiments, the ketamine is administered at least once a week, at least twice a week, at least three times per week, or more frequently. In another embodiment, the ketamine is administered at least twice per months, or at least once per months. Treatment can continue as long as needed.

Typically, a subject suffering from PTSD was exposed to a traumatic event in which the person experienced, witnessed, or was confronted with an event or events that involved actual or threatened death or serious injury, or a threat to the physical integrity of self or others and the person's response involved intense fear, helplessness, or horror. Typically, the traumatic event is persistently re-experienced in one or more of the following ways: recurrent and intrusive distressing recollections of the event, including images, thoughts, or perceptions, recurrent distressing dreams of the event, acting or feeling as if the traumatic event were recurring (includes a sense of reliving the experience, illusions, hallucinations, and dissociative flashback episodes, including those that occur on awakening or when intoxicated), intense psychological distress at exposure to internal or external cues that symbolize or resemble an aspect of the traumatic event, physiological reactivity on exposure to internal or external cues that symbolize or resemble an aspect of the traumatic event. An individual suffering from PTSD also has persistent avoidance of stimuli associated with the trauma and numbing of general responsiveness (not present before the trauma), as indicated by 3 or more of the following: efforts to avoid thoughts, feelings, or conversations associated with the trauma, efforts to avoid activities, places, or people that arouse recollections of the trauma, inability to recall an important aspect of the trauma, significantly diminished interest or participation in significant activities, feeling of detachment or estrangement from others, restricted range of affect (e.g., unable to have loving feelings), sense of a foreshortened future (e.g., does not expect to have a career, marriage, children, or a normal life span), persistent symptoms of increased arousal (not present before the trauma), as indicated by 2 or more of the following: difficulty falling or staying asleep, irritability or outbursts of anger, difficulty concentrating, hypervigilance, exaggerated startle response. The disturbance, which has lasted for at least a month, causes clinically significant distress or impairment in social, occupational, or other important areas of functioning. The symptoms expected to be decreased following treatment with ketamine include re-experiencing of the traumatic experience in the form of intrusive memories, nightmares, flashbacks, and emotional and physical reactions triggered by reminders of the trauma; distancing from others, decreased interest in activities and other people, numbing of feelings, and avoidance of trauma reminders; and hyperarousal symptoms, including disrupted sleep, irritability, hypervigilance, decreased concentration, and increased startle reflex.

In certain embodiments, it can be determined whether a method for treating PTSD, as disclosed herein, is effective, by determining whether one or more symptoms of PTSD is reduced or eliminated. Psychiatric evaluations of a patient being treated with a therapy disclosed herein can be conducted to determine whether the therapy (e.g., IV or intranasal administration of ketamine) is effective. In certain embodiments, the psychiatric evaluation may be carried out before treatment, at the time of treatment, during treatment, and/or after treatment. When the psychiatric evaluation is carried out both before treatment and after (and/or during) treatment with a therapy as disclosed herein. The results of the evaluation before treatment can provide a baseline for comparison to the results of the evaluation during and/or after treatment. However, in some embodiments, psychiatric evaluation is conducted only after treatment.

The methods for using ketamine to treat PTSD described herein may also be used to treat co-morbid conditions that respond to ketamine. Major depressive disorder, for example, exhibits co-morbidity with PTSD. In certain embodiments, for example, the methods described herein can thus be used to treat co-morbid PTSD and major depressive disorder.

By way of example, any one or more of the following psychiatric evaluations of a patient, which are well known in the art, can be conducted before and/or after administration of ketamine in order to determine whether PTSD has been treated. Examples of psychiatric evaluation tools and questionnaires used to evaluate PTSD and PTSD symptoms are as follows:

Measures

Both clinician-administered and validated self-report instruments are used, with the aim of measuring baseline symptomatology as well as drug actions on (1) the overall severity of the disorder, (2) the core symptoms of PTSD, and (3) depressed mood. Below is a description of the instruments used. Table 4 provides an overview.

The Diagnostic and Statistical Manual of Mental Disorders (DSM-5) includes the revised diagnostic criteria for PTSD. See, American Psychiatric Association: Diagnostic and Statistical Manual of Mental Disorders, Fifth Edition. Arlington, Va., American Psychiatric Association, 2013. See also ptsd.va.gov/professional/PTSD-overview/dsm5_criteria_ptsd.asp on the WorldWideWeb.

The Structured Clinical Interview for DSM-IV Axis I Disorders, Patient Edition (SCID-P) is a semi-structured interview that provides probe questions as well as follow-up questions to be asked by the clinician to assist in diagnosis. First et al., Structured Clinical Interview for DSM-IV TR Axis I Disorders, Research Version, Patient Edition (SCID-I/P). New York: New York State Psychiatric Institute, Biometrics Research; 2001. It includes an overview to obtain information about demographics, work, chief complaint, history of present illness, past history, treatment history, and current functioning. The main body of SCID-P includes 9 modules that are designed to diagnose 51 mental illnesses in all.

The SCID-P for DSM-5 is the SCID-Patient version, and is the next edition of the SCID modified to incorporate the new DSM-5 criteria.

The Clinician-Administered PTSD Scale (CAPS) is a structured clinical interview designed to assess the essential features of PTSD as defined by the DSM-IV. Weathers et al., Clinician-administered PTSD scale: a review of the first ten years of research. Depress Anxiety. 2001; 13(3):132-156. The CAPS can be used to provide categorical ratings of diagnostic status as well as a quantitative index of symptom severity. Both frequency and intensity scores are derived for each individual symptom. The CAPS total score is based on an individual's response to the 17 items that assess the frequency and intensity of current PTSD symptoms. Subscales of the CAPS are utilized to assess specific symptom clusters. Our research group has extensive experience using the CAPS from ongoing PTSD studies. The total score can range from 0 to 136.

The Clinician-Administered PTSD Scale for DSM-5 (CAPS-5) is a 30-item structured interview that can be used to make current (past month) diagnosis of PTSD, make lifetime diagnosis of PTSD, and to assess PTSD symptoms over the past week. CAPS-5 is a 30-item questionnaire, corresponding to the DSM-5 diagnosis for PTSD. The language of the CAPS-5 reflects both changes to existing symptoms and the addition of new symptoms in DSM-5.

CAPS-5 asks questions relevant to assessing the dissociative subtype of PTSD (depersonalization and derealization), but no longer includes other associated symptoms (e.g., gaps in awareness). As with previous versions of the CAPS, CAPS-5 symptom severity ratings are based on symptom frequency and intensity (except for amnesia and diminished interest which are based on amount and intensity). However, CAPS-5 items are rated with a single severity score in contrast to previous versions of the CAPS which required separate frequency and intensity scores. See Weathers, F. W., et al (2013). The Clinician-Administered PTSD Scale for DSM-5 (CAPS-5). Interview available from the National Center for PTSD at ptsd.va.gov on the WorldWideWeb.

The Treatment Outcome PTSD Scale (TOP-8) is a brief interviewer-administered scale designed specifically for the assessment of commonly occurring signs and symptoms of PTSD that are subject to change in response to treatment (Davidson, J. R., & Colket, J. T. (1997). The eight-item treatment-outcome post-traumatic stress disorder scale: A brief measure to assess treatment outcome in post-traumatic stress disorder. International Clinical Psychopharmacology, 12(1), 41-45). The TOP-8 is comprised of eight items, each measured on a scale of 0-4, with defined anchors given for each item. The items are representative of the three core features of PTSD with a maximum possible score of 32.

The Hamilton Psychiatric Rating Scale for Anxiety (HAM-A) is a widely used observational rating measure of anxiety severity. The scale consists of 14 items. Each item is rated on a scale of 0 to 4. This scale is administered to assess the severity of anxiety and its improvement during the course of treatment. The HAM-A total score is the sum of the 14 items and the score ranges from 0 to 56. Hamilton M. The Assessment of Anxiety-States by Rating. Br J Med Psychol. 1959; 32(1):50-55.

The Montgomery-Asberg Depression Rating Scale (MADRS) is a 10-item instrument used for the evaluation of depressive symptoms in adults and for the assessment of any changes to those symptoms. Montgomery S. A., et al., A new depression scale designed to be sensitive to change. Br J Psychiatry. 1979 April; 134:382-389. Each of the 10 items is rated on a scale of 0 to 6, with differing descriptors for each item. These individual item scores are added together to form a total score, which can range between 0 and 60 points. The estimated time to administer this scale is 20 minutes. Inter-rater reliability of the scale is high and scores correlate significantly with those of the HAM-D. On the infusion days a modified MADRS is used that excludes the sleep and appetite items.

The Young Mania Rating Scale, item 1 (YMRS-1) used to assess mood elevation on the infusion days. Young R C, et al. Rating-Scale for Mania—Reliability, Validity and Sensitivity. Br J Psychiatry. 1978; 133 (November):429-435.

The Brief Psychiatric Rating Scale (BPRS) is used to assess acute behavioral changes during the infusions. Overall J E et al., The Brief Psychiatric Rating-Scale. Psychol Rep. 1962; 10(3):799-812 Four key BPRS items for the positive (+) symptoms of psychosis are used: conceptual disorganization, hallucinatory behavior, suspiciousness, and unusual thought content. Three items representing the negative (−) symptoms of psychosis will also be used: blunted affect, emotional withdrawal, and motor retardation.

The Clinician-Administered Dissociative States Scale (CADSS) is used to measure dissociative effects during the infusions. Bremner J D, et al., Measurement of Dissociative States with the Clinician-Administered Dissociative States Scale (CADSS). J Trauma Stress. 1998; 11(1):125-136 The scale includes 19 questions and 8 observer ratings scored from 0 (not at all) to 4 (extremely). The CADSS measures impairment in body perception, environmental perception, time perception, memory impairment, and feelings of unreality.

The Patient Rating Inventory of Side Effects (PRISE) is a patient self-report used to qualify side effects by identifying and evaluating the tolerability of each symptom. Levine J, Schooler N R. SAFTEE: A technique for the systematic assessment of side effects in clinical trials. Psychopharmacol Bull. 1986; 22(2):343-381.

The Clinical Global Impression (CGI) scale assesses treatment response in psychiatric patients. The administration time is 2 minutes. This scale consists of three items: Severity of Illness (item 1); Global Improvement (item 2); and Efficacy Index (item 3). Item 1 is rated on a seven-point scale (1=normal, 7=among the most extremely ill patients) as is item 2 (1=very much improved, 7=very much worse). Each includes an additional response of "not assessed." Item 3 is rated on a four-point scale (from "none" to "outweighs therapeutic effect"). Only items 1 (CGI-Severity or CGI-S) and 2 (CGI-Improvement or CGI-I) are used.

The Impact of Events Scale (IES) is one of the most widely used self-report measures of stress reactions to traumatic events. Horowitz M, Wilner N, Alvarez W. Impact of Event Scale: a measure of subjective stress. Psychosom Med. 1979 May; 41(3):209-218. See also, Weiss D S, Marmar C R. The Impact of Event Scale—Revised In: Wilson J, Keane T M, eds. Assessing psychological trauma and PTSD. New York: Guilford; 1996:399-411. It measures both intrusion and avoidance. A 2002 review that evaluated its psychometric properties revealed high internal consistencies for both subscales (intrusion: mean $\alpha$=0.86; avoidance: mean $\alpha$=0.82), adequate test-retest reliability for intervals of >1 year, and good internal and external validity. Sundin E C, Horowitz M J. Impact of Event Scale: psychometric properties. Br J Psychiatry. 2002 March; 180:205-209. Correlations between IES subscales and PTSD diagnosis assessed with the CAPS are high (>0.75). Id. The IES is considered particularly useful as a measure of the intrusive and avoidant processes that mediate between the experience of trauma and subsequent adjustment. Joseph S. Psychometric evaluation of Horowitz's Impact of Event Scale: a review. J Trauma Stress. 2000 January; 13(1):101-113. The total score can range from 0 to 75.

The Posttraumatic Stress Disorder Checklist (PCL-5) is a 17-item self-report measure reflecting DSM-5 symptoms of PTSD. The PCL-5 measures symptoms in response to stressful situations (Weathers, F., et al. (1993). The PTSD checklist (PCL): Reliability, validity, and diagnostic utility. Annual Convention of the International Society for Traumatic Stress Studies, San Antonia, Tex.).

The Quick Inventory of Depressive Symptomatology, Self Report (QIDS-SR) is a 16-item self rated instrument designed to assess the severity of depressive symptoms present in the past seven days. Rush A J, Trivedi M H, Ibrahim H M et al. The 16-Item quick inventory of depressive symptomatology (QIDS), clinician rating (QIDS-C), and self-report (QIDS-SR): a psychometric evaluation in patients with chronic major depression. Biol Psychiatry. 2003; 54(5):573-583. The 16 items cover the nine symptom domains of major depression, and are rated on a scale of 0-3. Total score ranges from 0 to 27, with ranges of 0-5 (normal), 6-10 (mild), 11-15 (moderate), 16-20 (moderate to severe), and 21+(severe).

The Childhood Trauma Questionnaire (CTQ) is a 28-item self-report instrument that assesses childhood trauma in the following areas: physical, sexual and emotional abuse and physical and emotional neglect. Bernstein D P, Stein J A, Newcomb M D et al. Development and validation of a brief screening version of the Childhood Trauma Questionnaire. Child Abuse Negl. 2003 February; 27(2):169-190. Each item is rated on a scale of 1 (never true) to 5 (very often true). The 5 subscales are then totaled, with scores ranging from 5-25 for each traumatic category.

Visual Analogue Scales (VAS) are used to assess subjective state changes. Bond A, Lader M. The use of analogue scales in rating subjective feelings. Br J Med Psychol. 1974; 47(3):211-218. They are 100-mm horizontal lines marked proportionately to the perceived intensity of the subjective experience (0=not at all, to 10=extremely) for the following states: anxious, depressed, drowsy, high, hungry, and nauseous.

The Sheehan Disability Scale (SDS) is the most frequently used self-report disability measure. It has demonstrated sensitivity to impairment and changes as a result of treatment across a wide range of psychiatric disorders. The SDS asks only about current levels of impairment, providing no indication of whether the person has done better or worse in the past, thus making it a reasonable short-term outcome measure that is un-confounded by historical impressions. The dependent variable is the total score, which is based on the sum of three 10-point items (work, social life, and family life), with higher scores reflecting greater disability. Sheehan D. The Anxiety Disease. New York, N.Y.: Scribner; 1983.

The Connor-Davidson Resilience Scale (CD-RISC) is a 25-item self-report scale, each rated on a 5-point scale (0-4), with higher scores reflecting greater resilience (Connor K M & Davidson, J R T. Development of a new resilience scale: the Connor-Davidson Resilience Scale (CD-RISC). Depression and Anxiety, 2003: 18: 71-82).

The Wechsler Abbreviated Scale of Intelligence 2-Subtest (WASI-2) is a reliable brief measure of IQ for 6 to 89 year-olds that takes 15 minutes to complete and includes Vocabulary (an estimate of verbal fluid abilities) and Matrix Reasoning (an estimate of nonverbal fluid abilities). Wechsler D. Wechsler Abbreviated Scale of Intelligence San Antonio, Tex.: Psychological Corporation; 1999. It is extensively used in clinical, educational, and research settings. Average reliability coefficient is 0.96 and test-retest reliability is 0.88.

The Hopkins Verbal Learning Test (HVLT) is a repeatable test of memory acquisition and delayed recall of words. Subjects are presented with the same 12-item list for 3 learning trials and asked each time to repeat the items on each list. Delayed recall and recognition conditions are administered later. Dependent variables used in this study include total learning over the 3 trials (for the acquisition variable) and total delayed recall score (for the recall component). Brandt J, Benedict R. Hopkins Verbal Learning Test, Revised. Odessa, Fla.: Psychological Assessment Resources; 1997.

The Profile of Mood States-Bipolar (POMS-Bi) scale measures moods and feelings primarily in clinical rather than nonclinical settings. It can help to determine an individual's psychiatric status for therapy, or be used to compare mood profiles associated with various personality disorders. It is also a useful instrument in identifying the effects of drug treatments.

The Post-Traumatic Cognitions Inventory (PTCI) is a 33-item scale, which is rated on a Likert-type scale ranging from 1 (totally disagree) to 7 (totally agree). Scale scores are formed for the three subscales, which show a high degree of intercorrelation (rs=0.57-0.75).

The New Cognitions scale is a 6-item pilot scale, which is rated on a Likert-type scale ranging from 1 (not at all) to 4 (a lot). The scale is based on the Post Traumatic Growth Inventory (PTGI) from which items have been directly selected (new items were added to the scale as well), and on the Brief-COPE (see Carver, C. S. (1997) "You want to measure coping but your protocol's too long: Consider the brief COPE." International Journal of Behavioral Medicine 4; 92-100).

The Medical Outcomes Study (MOS) Social Support Survey is a 19-item self-report measure designed to assess levels of functional social support. The MOS-SS has two subscales (emotional and instrumental social support) to identify potential social support deficits (Sherbourne, C. D. & Stewart, A. L. (1991). "The MOS Social Support Survey." Soc Sci Med 32(6): 705-714).

The Purpose in Life test-Short Form (PIL-SF) is a brief, 4-item form of the 20-item Purpose in Life test. This scale asks respondents to report to what extent they have achieved their goals in life, and to what extent they perceive their life to be meaningful or purposeful. (Schulenberg et al 2010; Psychotherapy (Chic). 2008 December; 45(4):447-63).

Posttraumatic Growth Inventory (PTGI)-Short Version is a 10-item shortened version of the PTGI self-report questionnaire (ref). It asks respondents to rate the extent to which they have changed as the result of experiencing a highly stressful life event. Items span positive changes in five domains: relating to others, new possibilities, personal strength, spiritual change, and appreciation of life (Cann, A., et al. (2010). A short form of the Posttraumatic Growth Inventory. Anxiety, Stress & Coping, 23, 127-137).

The Quality of Life Enjoyment and Satisfaction Questionnaire (Q-LES-Q) is a self-report scale measuring the degree of enjoyment and satisfaction experienced by subjects in various areas of daily functioning. The summary scores are reliable and valid measures of these dimensions in a group of depressed subjects (Endicott J, et al. Quality of Life Enjoyment and Satisfaction Questionnaire: A New Measure. Psychopharmacology Bulletin; 1993; 29:321-326).

In other embodiments, determining whether a therapy disclosed herein is effective for treating PTSD can be based on the self-evaluation of the patient being treated, e.g., if the patient reports that one or more symptoms of his or her PTSD has been treated.

Typically, the effects of treatment with a composition or formulation disclosed herein are observed by the patient and/or, e.g., the patient's physician, within a predetermined time frame from the time of administration. Typically, the predetermined time frame is starting within 2 hours of the administration and up to 24 hours of the administration of the composition or formulation. In other embodiments, the predetermined time frame is within 0.5 hours, 1 hour, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 10.5 hours, 11 hours, 11.5 hours, 12 hours, 18 hours, 24 hours, 48 hours, or 72 hours following administration of the composition or formulation.

In yet other embodiments, the predetermined time frame is within 1 day, 2 days, 3 days, 4 days, 5 days, 6 days, 7 days, or 14 days following administration of the composition or formulation.

In still other embodiments, the predetermined time frame is within 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, or 30 minutes following administration of the composition or formulation.
Predictive Value of Ketamine-Induced Memory Impairments on Outcome Having repeated intrusive memories of the trauma exposure is one of the core symptoms of PTSD. Patients with PTSD are known to display impairments in learning and memory during neuropsychological testing. These memory disturbances may be at least partially due to dysregulation in glutamatergic pathways. Further, experimental studies have shown memory disruption during ketamine infusion, which is thought to result from interference with the retrieval processes necessary for recall. This effect likely includes glutamatergic action on the hippocampus. The acute effects of IV ketamine on memory in patients with PTSD block their distressing intrusive memories, or at least the emotional content associated with it. The extent of memory impairment induced by ketamine (measured using the Hopkins Verbal Learning Test or HVLT) on the infusion days may be a positive predictor of outcome.

EXAMPLES

The present disclosure is described further below in working examples which are intended to further describe the invention without limiting the scope therein.

Example 1: Intravenous Ketamine Treatment of PTSD: Case Studies

In a ketamine infusion study in patients with treatment resistant depression (TRD), ketamine (0.5 mg/kg IV) was administered open-label and combined with pre-infusion treatment with a single oral dose of lamotrigine (300 mg) or placebo administered under double-blind conditions. Preliminary analyses were recently performed on a sample of 16 patients. Ketamine reduced clinical depression scores, as measured using the percentage reduction in Montgomery-Asberg Depression Rating Scale (MADRS) scores from baseline to 24 hours post-infusion. Self-reported mood also improved, as measured using the Quick Inventory of Depressive Symptoms, Self-Report version (QIDS-SR). A strong positive correlation between individual childhood trauma (abuse and/or neglect) and the antidepressant response (MADRS: $r=0.55$, $p=0.03$; QIDS-SR: $r=0.59$, $p=0.02$).

The effect of ketamine on Hamilton Anxiety Rating Scale (HAM-A) scores was also measured. A strong positive correlation between the magnitude of the ketamine-induced reduction in HAM-A scores and personal history of childhood trauma measured using the Childhood Trauma Questionnaire (CTQ; $n=15$, $r=0.59$, $p=0.02$) was observed. In view of these results, a possible role of trauma in the therapeutic efficacy of ketamine was further investigated. Two of the four TRD patients with the highest CTQ thus far had a co-morbid current PTSD diagnosis. Patient A, suffered from distressing intrusive memories, nightmares, flashbacks, hypervigilance, poor concentration, and depressed mood. Patient A described her PTSD and MDD symptoms as chronic, but having intensified over time, due to ongoing events in her life. Patient A had a CTQ score of 81 at baseline. During ketamine infusion, when queried about feelings of guilt and worthlessness, Patient A exhibited a striking, almost instantaneous cognitive revision of adverse events in her life.

After observing the magnitude of the therapeutic effect of ketamine in Patient A, TRD patients with a co-morbid current PTSD diagnosis were administered the Clinician-Administered PTSD Scale (CAPS) and the Impact of Events Scale (IES) before and after ketamine infusion. Patient M had a CTQ score of 108, a CAPS score of 81 (out of 136) and an IES score of 48 (out of 75). The day after ketamine infusion, Patient M reported that he felt an "intellectual distance" from the emotional content of prior traumatic events that allowed him to feel more in control. Patient M further described feeling relieved of a compulsion to continuously analyze his past, identify ways in which he might have circumvented trauma, and subsequently punish himself for his failure to avoid trauma. One week post-infusion, Patient M's CAPS score had dropped by 90% and could be considered a remission (defined as CAPS<20). Two weeks post-infusion, Patient M maintained his "intellectual distance" from the emotional content associated with his trauma. Patient M's baseline and post-infusion IES scores presented in Table 1.

TABLE 1

| | CAPS | IES |
|---|---|---|
| Baseline (pre-ketamine) | 81 | 48 |
| +40 min (post-ketamine) | | 33 |
| +240 min | | 3 |
| +24 hours | | 16 |
| +72 hours | | 5 |
| +1 week | 8 | 5 |
| +2 weeks | 27 | 15 |

Patients A and M were the two patients with the largest ketamine-induced percentage reductions in MADRS, QIDS-SR and HAM-A scores in the entire sample.

Example 2: Intravenous Ketamine Treatment of PTSD: Controlled Study

This Example demonstrates that IV administered ketamine inhibited the symptoms of PTSD. In patients with co-morbid major depressive disorder, IV administration of ketamine inhibited symptoms of both PTSD and MDD.

Patients with chronic PTSD were enrolled in a controlled study. Eligible participants were between 18 and 55 years of age, had a primary diagnosis of PTSD assessed with the Structured Clinical Interview for DSM-IV-TR Axis I Disorders-Patient Version (SCID-I/P) (First et al., supra) and a score of at least 50 on the Clinician-Administered PTSD Scale (CAPS) (Weathers et al., supra). Exclusion criteria included lifetime history of psychotic or bipolar disorder, current bulimia or anorexia nervosa, alcohol abuse or dependence in the previous three months, serious unstable medical illness or sleep apnea, active suicidal or homicidal ideation on presentation, or current use of any psychotropic medications. All patients underwent a physical examination and laboratory screening including routine hematologic, biochemical and urine toxicology testing, as well as an electrocardiogram to rule out unstable medical illness and active substance use. To receive the second IV infusion, a CAPS score of at least 50 was required prior to the second infusion. The Institutional Review Board at Mount Sinai approved the study, and informed consent was obtained from all study participants.

Procedures

Study participants were free of concomitant psychotropic medications for two weeks prior to randomization and for the duration of the study. For each procedure day, patients were assigned to receive a single IV infusion of ketamine hydrochloride (0.5 mg/kg) or midazolam (0.045 mg/kg), administered over 40 minutes. Order of infusions (ketamine-midazolam or midazolam-ketamine) was randomly assigned and administrations were two weeks apart. Midazolam was chosen as the active placebo control because its pharmacokinetic parameters and non-specific behavioral effects are similar to those of ketamine. Only the research pharmacy was aware of drug identity, and all study personnel, including investigators, anesthesiologists, raters, patients and data analysts were blinded to randomization order.

Following admission and an overnight fast, an indwelling catheter was placed in the antecubital vein of the non-dominant arm. Pulse, blood pressure, pulse-oximetry and ECG monitoring were instituted (see Murrough J et al. Antidepressant efficacy of ketamine in treatment-resistant major depression: a two-site, randomized controlled trial. The American Journal of Psychiatry. 2013 Oct. 1; 170(10): 1134-42). Ratings were administered by a trained rater during the infusion and at 240 minutes after the start of the infusion. A different rater, blinded to the ratings during post-infusion on infusion, administered ratings at pre-infusion baseline, 24 hours (Day 1) post-infusion (before patients were discharged from the hospital), 48 hours (Day 2), 72 hours (Day 3), and 7 days (Day 7) post-infusion. Ratings were also administered at 10 and 13 days post-infusion, though data analyses focused on the first week post-infusion due to the expected duration of ketamine action. Patients were instructed to abstain from taking psychotropic medications and from using alcohol or substances of abuse for the duration of the trial. As described above, patients who scored≥50 on the CAPS 2 weeks after the first infusion received an infusion of the second study drug. Patients whose symptoms remained significantly improved at 2 weeks post-infusion, indicated by a score<50 at 2 weeks, were considered to have completed the study after one infusion.

Outcomes

The primary outcome was PTSD symptom severity at 24 hours post-infusion, assessed with the Impact of Event Scale-Revised (IES-R). Twenty-four hours post-infusion was selected as the primary endpoint, as acute sedating and other side effects were expected to have resolved, while potential symptom improvement was expected to persist at 24 hours. Secondary outcome measures included the Montgomery-Asberg Depression Rating Scale (MADRS), the Quick Inventory of Depressive Symptomatology, Self-Report (QIDS-SR), and Clinical Global Impression-Severity (CGI-S) and -Improvement (GCI-I) scales administered by a study clinician at 24 hours, 48 hours, 72 hours and 7 days post-infusion. The IES-R was also administered at 48 hours, 72 hours, and 7 days post-infusion. Additionally, the CAPS was administered 7 days post-infusion.

General side effects and possible dissociative, psychotomimetic, and manic symptoms were measured with the Patient-Rated Inventory of Side Effects (PRISE), Clinician-Administered Dissociative States Scale (CADSS), Brief Psychiatric Rating Scale (BPRS) and Young Mania Rating Scale (YMRS) item 1 (elevated mood), respectively.

Statistical Analysis

The ability of ketamine to reduce PTSD symptoms was assessed in a proof-of-concept randomized, double-blind, active placebo control (midazolam) crossover trial. A total of 41 patients were enrolled, with order of treatment determined by randomization. The primary analysis adhered to a modified intention-to-treat principle, including all 29 patients with outcome assessments from both periods. A mixed-model approach was employed to test effects of treatment, period, and carryover. An additional intention-to-treat analysis of covariance, adjusting for baseline IES-R, was conducted with all 41 patients using only first-period data. All statistical tests were two-sided 0.05 level tests. Secondary analyses of additional endpoints followed the same analytic approach as for the primary endpoint. No adjustment for multiple tests was employed; all p-values are reported at their nominal level. The primary interest was on changes in symptom outcomes observed during the first week, given the hypothesized duration of the effects of ketamine. A planned sample size of 40 patients randomly assigned to treatment order was estimated to provide 80% power to detect a treatment difference in change in IES-R scores of 0.9 standard deviation units at 24 hours post-infusion.

Secondary analyses also examined the effect of depression on PTSD symptoms and the interaction between treatment and depression. A mixed model approach was used to examine the effects of treatment, baseline MADRS score, and 24-hour MADRS score using only first-period data. Safety and tolerability were analyzed using descriptive statistics.

Of 57 potential participants who completed informed consent procedures, 41 met eligibility criteria and were randomized to receive ketamine or midazolam during the first infusion. All 41 patients received study medication and completed 24-hour ratings; 29 of them completed both infusions and ratings following each infusion. Of the remaining 12 participants, 6 (all of whom had been randomized to receive ketamine first) completed the study at 2 weeks, following only their first infusion and ratings, because their CAPS scores were <50 at 2 weeks, precluding the second administration. Two additional participants also had a CAPS score<50 at 2 weeks, one who received ketamine first and the other midazolam first, but received their second infusion a week later. See Tables 2 and 3, below.

TABLE 2

Ketamine responders who remained much improved 2 weeks later

| IES-R Total (Baseline) | IES-R Total (Week 1) | IES-R Total (Day 10) | IES-R Total (Week 2) | CAPS Total (Baseline) | CAPS Total (Week 1) | CAPS Total (Week 2) | CGI-I (Week 1) | CGI-I (Week 2) |
|---|---|---|---|---|---|---|---|---|
| 60 | 18 | 25.14 | 26 | 97 | 54 | 44 | 2 | — |
| 54 | 17 | 28 | 28 | 83 | 22 | 45 | 2 | — |
| 24 | 3 | 3 | 2 | 60 | 13 | 11 | 2 | 2 |
| 15 | 1 | 4 | 6 | 52 | 16 | 11 | 2 | 2 |
| 19 | 8.38 | 3 | 1 | 71 | 45 | 25 | — | — |
| 59 | 10 | 15 | 14 | 93 | 41 | 28 | 2 | 2 |
| 17 | 2 | 3 | 0 | 73 | 33 | 19 | 3 | 3 |

TABLE 3

Midazolam responder who remained much improved 1 week later:

| 43 | 12.57 | 6 | 5 | 62 | 50 | 30 | 4 | 4 |
|----|-------|---|---|----|----|----|----|---|

Demographic and Clinical Characteristics

Table 4 summarizes demographic, trauma exposure and clinical characteristics of patients randomized to receive ketamine or midazolam. All patients had chronic PTSD, most persisting for several years, with moderate to severe symptoms (see Table 4). Fewer than 50% of participants had received psychotropic medication in the past, generally one or two antidepressants with partial or no response though occasionally with good response, and few had received additional medications such as a benzodiazepine, a sedative-hypnotic, prazosin or an atypical antipsychotic. Prior to beginning study procedures, only two patients required psychotropic medication taper, one from topiramate and the other from amphetamine/dextroamphetamine mixed salts.

TABLE 4

| Characteristic | Ketamine[a] (n = 22) | Midazolam[b] (n = 19) |
|---|---|---|
| Mean age in years (SD) | 36.4 (10.8) | 35.7 (10.0) |
| Female sex - n (%) | 13 (59.1%) | 6 (32.0%) |
| Race | | |
| Black - n (%) | 11 (50.0%) | 12 (63.2%) |
| White - n (%) | 5 (22.7%) | 2 (10.5%) |
| Other - n (%) | 6 (27.3%) | 5 (26.3%) |
| Hispanic ethnicity - n (%) | 5 (22.7%) | 0 |
| Years of education (SD) | 4.6 (1.5) | 4.3 (1.1) |
| Unemployed - n (%) | 11 (50.0%) | 14 (73.7%) |
| Married or cohabiting - n (%) | 5 (22.7%) | 3 (15.8%) |
| Primary trauma | | |
| Sexual assault or molestation - n (%) | 9 (40.9%) | 4 (21.1%) |
| Physical assault or abuse - n (%) | 4 (18.2%) | 7 (36.8%) |
| Accident or fire - n (%) | 1 (4.5%) | 3 (15.8%) |
| Combat exposure - n (%) | 2 (9.1%) | 0 |
| Witnessed violent assault or death - n (%) | 4 (18.2%) | 5 (26.3%) |
| Witnessed 9/11 terrorist attacks - n (%) | 2 (9.1%) | 0 |
| Duration of PTSD in years (SD) | 14.2 (12.3) | 11.9 (14.0) |
| History of treatment with psychotropic medication - n (%) | 11 (50.0%) | 8 (42.1%) |
| CAPS score (past month) (SD) | 82.5 (14.1) | 77.1 (11.8) |
| QIDS-SR score (SD) | 12.4 (5.2) | 11.3 (5.6)[c] |

Legend:
[a]Patients randomized to receive ketamine first;
[b]Patients randomized to receive midazolam first;
[c]n = 15 as QIDS-SR scores are missing in 4 participants;
SD = standard deviation;
PTSD = posttraumatic stress disorder;
CAPS = Clinician Administered PTSD scale;
QIDS-SR = Quick Inventory of Depressive Symptomatology, Self-Report version.

Primary Outcome

In the crossover analysis, total IES-R scores 24 hours post-infusion were significantly improved with ketamine compared to midazolam [mean difference=12.7, 95% confidence interval (CI)=2.5-22.8, p=0.017] (FIG. 1A). There was no evidence of any period or residual effects for the crossover. Additionally, 7 patients randomized to ketamine first remained significantly improved post-infusion, compared to only one patient randomized to midazolam first. Analysis of IES-R scores at 24 hours based on the first period only, including all 41 randomized patients, agreed closely (mean difference=8.6, 95% CI=0.94-16.2, p=0.029) (FIG. 1A). Neither MDD diagnosis at screening nor MADRS score at pre-infusion baseline had a significant effect on the change in IES-R score at 24 hours (FIGS. 1A, 1C).

Secondary Outcomes

Additional Twenty-Four-Hour Outcomes and CAPS at 7 days

In crossover analyses with 29 patients, the CGI-S and CGI-I scores at 24 hours were also significantly better following ketamine (see FIG. 1, Table 5).

TABLE 5

Clinical Improvement at 24 Hours in IES-R Score and Secondary Outcomes - Cross-Over and First Infusion Results

| Measure | Cross-over 24 hours n = 29 | | | First infusion 24 hours n = 41 | | |
|---|---|---|---|---|---|---|
| | Mean difference | 95% CI | p value | Mean difference | 95% CI | p value |
| IES-R total[a] | 12.7 | 2.5-22.8 | 0.017 | 8.6 | 0.94-16.2 | 0.029 |
| Re-experiencing | 4.0 | -0.26-8.3 | 0.065 | 2.6 | -0.80-6.0 | 0.13 |
| Avoidance | 4.8 | 0.18-9.3 | 0.042 | 3.3 | -0.71-6.8 | 0.055 |
| Hyperarousal | 3.9 | 0.56-7.2 | 0.023 | 2.6 | 0.21-4.9 | 0.034 |
| CGI-S | 1.0 | 0.10-1.9 | 0.03 | 0.90 | 0.32-1.5 | 0.003 |
| CGI-I | 1.2 | 0.46-1.9 | 0.003 | 0.80 | 0.24-1.3 | 0.005 |
| QIDS | 0.17 | -3.9-4.3 | 0.93 | 1.5 | -1.1-4.2 | 0.25 |
| MADRS | 3.7 | -7.5-14.9 | 0.51 | 2.7 | -1.7-7.1 | 0.23 |

Legend:
[a]Primary outcome measure;
IES-R = Impact of Event Scale-Revised;
CGI-S = Clinical Global Impression scale - Severity;
CGI-I = Clinical Global Impression scale - Improvement;
QIDS-SR = Quick Inventory of Depressive Symptomatology - Self-Report;
MADRS = Montgomery-Asberg Depression Rating Scale.

Analysis of CGI-S and CGI-I scores at 24 hours based on the first period only, including all 41 randomized patients, supported the findings from crossover analyses (see Table 3). Crossover analyses (29 patients) of MADRS and QIDS-SR at 24 hours did not yield any significant effect of ketamine treatment over the control condition. Mean CAPS score at 7 days post-infusion, did not differ significantly by treatment (mean difference ketamine-midazolam=8.7, 95% CI=−4.8-22.2, p-value=0.20). See Tables 6-9, below.

TABLE 6

Baseline, Week-1 and Week-2 IES-R, CAPS, and CGI-I scores, full sample

| Variable | Label | N | Mean | Std Dev | Minimum | Maximum |
|---|---|---|---|---|---|---|
| IES-R_baseline | IES-R Total (Baseline) | 35 | 48.44 | 16.61 | 15 | 74 |
| CAPS_baseline | CAPS Total (Baseline) | 35 | 80.09 | 12.36 | 52 | 100 |
| CGII_day7 | CGI-I (Week 1) | 33 | 3.489 | 0.97 | 2 | 5 |
| IES-R_day7 | IES-R Total (Week 1) | 34 | 30.42 | 17.71 | 1 | 63 |
| CAPS_day7 | CAPS Total (Week 1) | 35 | 59.34 | 21.18 | 13 | 94 |
| CGII_day13 | CGI-I (Week 2) | 24 | 3.50 | 0.88 | 2 | 5 |
| IES-R_day13 | IES-R Total (Week 2) | 32 | 28.66 | 16.32 | 0 | 61 |
| CAPS_day13 | CAPS Total (Week 2) | 35 | 62.89 | 24.86 | 11 | 103 |

Legend:
IES-R = Impact of Event Scale - Revised;
CAPS = Clinician-Administered PTSD Scale;
CGI-I = Clinical Global Impression - Improvement (the CGI-I is not administered at baseline);
Std Dev = standard deviation.

TABLE 7

Baseline, Week-1 and Week-2 IES-R, CAPS, and CGI-I scores, by treatment group, Randomization sequence = 1 (Ketamine first)

| Variable | Label | N | Mean | Std Dev | Minimum | Maximum |
|---|---|---|---|---|---|---|
| IES-R_baseline | IES-R Total (Baseline) | 19 | 44.84 | 20.13 | 15 | 74 |
| CAPS_baseline | CAPS Total (Baseline) | 19 | 81.42 | 13.96 | 52 | 100 |
| CGII_day7 | CGI-I (Week 1) | 18 | 3.22 | 1.06 | 2 | 5 |
| IES-R_day7 | IES-R Total (Week 1) | 19 | 25.76 | 19.40 | 1 | 63 |
| CAPS_day7 | CAPS Total (Week 1) | 19 | 54.00 | 23.63 | 13 | 90 |
| CGII_day13 | CGI-I (Week 2) | 13 | 3.15 | 0.80 | 2 | 4 |
| IES-R_day13 | IES-R Total (Week 2) | 18 | 25.67 | 17.77 | 0 | 61 |
| CAPS_day13 | CAPS Total (Week 2) | 19 | 56.21 | 28.43 | 11 | 103 |

Legend:
IES-R = Impact of Event Scale - Revised;
CAPS = Clinician-Administered PTSD Scale;
CGI-I = Clinical Global Impression - Improvement (the CGI-I is not administered at baseline);
Std Dev = standard deviation

TABLE 8

Randomization sequence = 2 (Midazolam first)

| Variable | Label | N | Mean | Std Dev | Minimum | Maximum |
|---|---|---|---|---|---|---|
| IES_baseline | IES-R Total (Baseline) | 16 | 52.70 | 10.16 | 32 | 72 |
| CAPS_baseline | CAPS Total (Baseline) | 16 | 78.50 | 10.36 | 57 | 95 |
| CGII_day7 | CGI-I (Week 1) | 15 | 3.80 | 0.77 | 2 | 5 |
| IES_day7 | IES-R Total (Week 1) | 15 | 36.32 | 13.73 | 11 | 53 |
| CAPS_day7 | CAPS Total (Week 1) | 16 | 65.69 | 16.36 | 31 | 94 |
| CGII_day13 | CGI-I (Week 2) | 11 | 3.91 | 0.83 | 2 | 5 |
| IES_day13 | IES-R Total (Week 2) | 14 | 32.51 | 13.92 | 5 | 51 |
| CAPS_day13 | CAPS Total (Week 2) | 16 | 70.81 | 17.55 | 30 | 99 |

Legend:
IES-R = Impact of Event Scale - Revised;
CAPS = Clinician-Administered PTSD Scale;
CGI-I = Clinical Global Impression - Improvement (the CGI-I is not administered at baseline);
Std Dev = standard deviation

TABLE 9

Frequency Table for Response[a] by Treatment
Table of IES-R_response by randomization sequence IES-R_response
Frequency
Percent
Row Pct         Randomization Sequence

| Col Pct | Ketamine first | Midazolam first | Total |
|---|---|---|---|
| No | 9 | 11 | 20 |
|  | 25.71 | 31.43 | 57.14 |
|  | 45.00 | 55.00 |  |
|  | 47.37 | 68.75 |  |
| Yes | 10 | 5 | 15 |
|  | 28.57 | 14.29 | 42.86 |
|  | 66.67 | 33.33 |  |
|  | 52.63 | 31.25 |  |
| Total | 19 | 16 | 35 |
|  | 54.29 | 45.71 | 100.00 |

Legend: [a]Response = 50% improvement in IES-R score at 24 hours post-infusion; 52.63% responded after ketamine infusion and 31.25% responded after midazolam infusion.

Comorbid Depressive Symptoms

In further period-1 analyses with all 41 patients, treatment assignment [$\beta$=6.5, p=0.0496], MADRS score at 24 hours post-infusion [$\beta$=0.9, p=0.0004], and baseline IES-R score [$\beta$=0.2, p=0.0418] were shown to have significant effects on the IES-R score at 24 hours post-infusion, with ketamine showing significantly better improvement than midazolam. Baseline MADRS and the interaction between 24-hour MADRS score and treatment were not significant predictors of IES-R score 24 hours post-infusion.

Durability of Drug Effect

General linear mixed modeling analyses of the first period only, including all 41 randomized patients, evaluated IES-R, MADRS and QIDS-SR scores at 24, 48, and 72 hours, and seven days post-infusion as a function of treatment, time and treatment-by-time interaction. Analyses demonstrated a significant effect of treatment on the IES-R and a significant effect of time on the IES-R, MADRS and QIDS-SR. The effect of treatment on the MADRS and QIDS-SR approached significance. There were no significant treatment-by-time interactions. Collapsing across time, patients who received ketamine demonstrated significantly lower mean IES-R scores than those who received midazolam (differences of least squares means estimate=−8.32, p=0.046), and lower MADRS (−3.99, p=0.052) and QIDS-SR (−2.73, p=0.050) scores approaching significance.

Figure 1B:
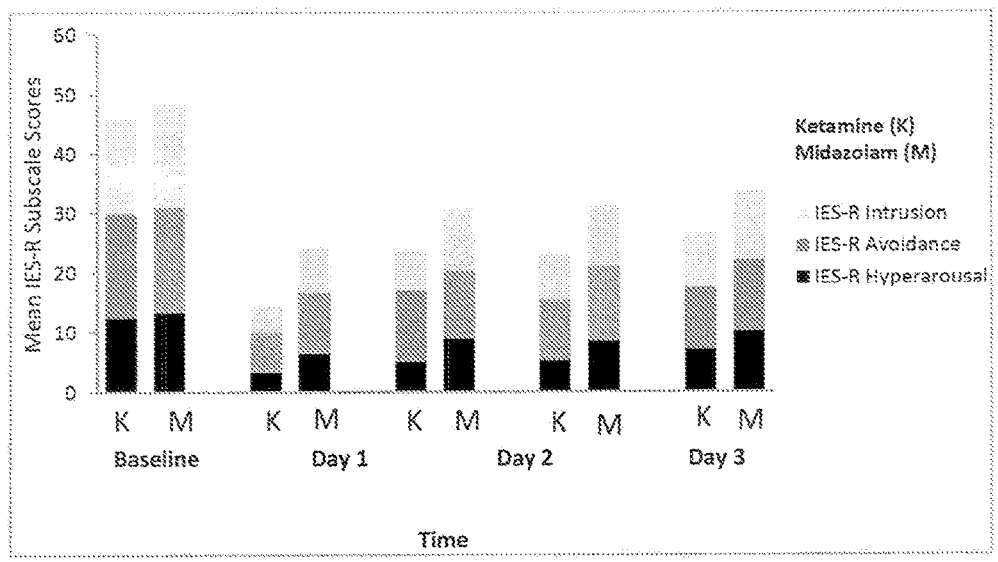
Figure 1C:
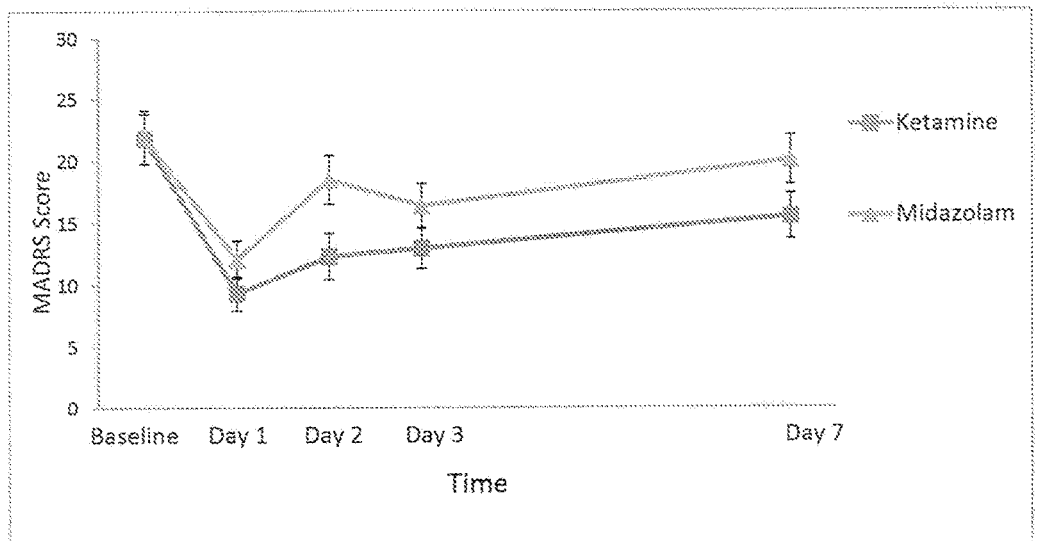

Ketamine had a similar effect on the three PTSD symptom clusters, measured by the IES-R subscales (Table 5 and FIG. 1B).

Adverse Events

Figure 2A:
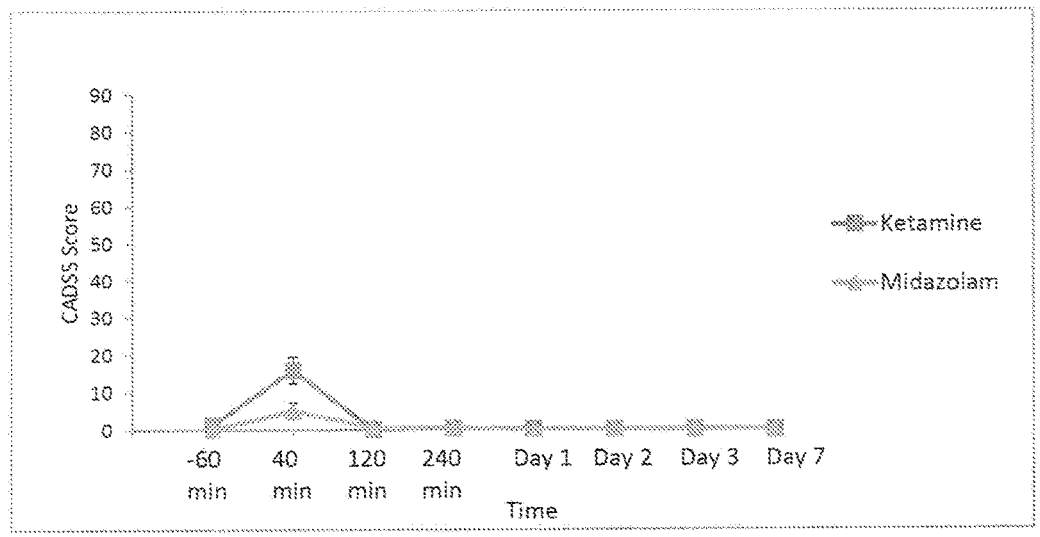
FIGS. 2A-2C contain line graphs quantifying the change in the Brief Psychiatric Rating Scale (BPRS) Positive Symptoms subscale score, the Clinician-Administered Dissociative States Scale (CADSS) score, and the Young Mania Rating Scale (YMRS) item 1 score over 1 week after the first infusion of ketamine or midazolam (n=41). Error bars represent standard errors).
Figure 2B:
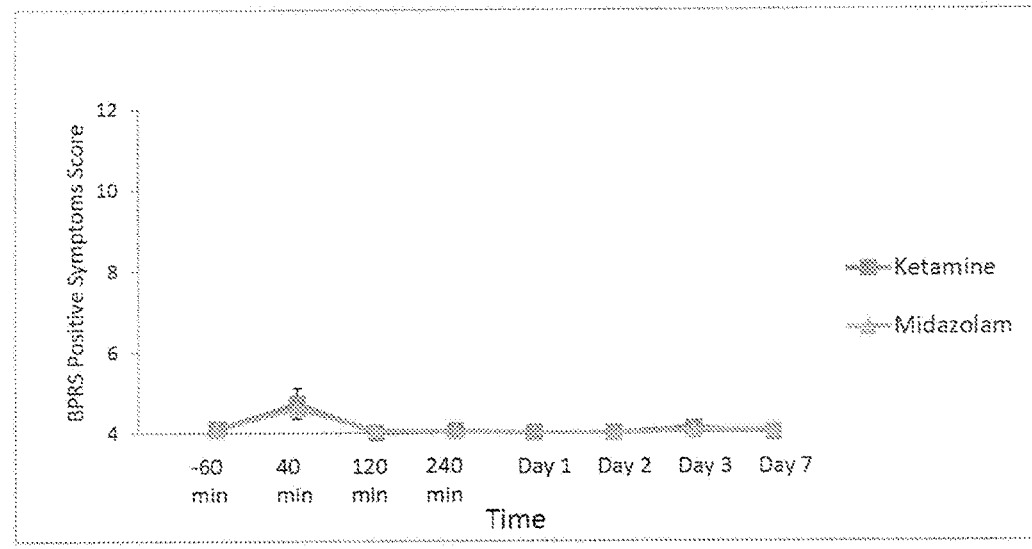
Figure 2C:
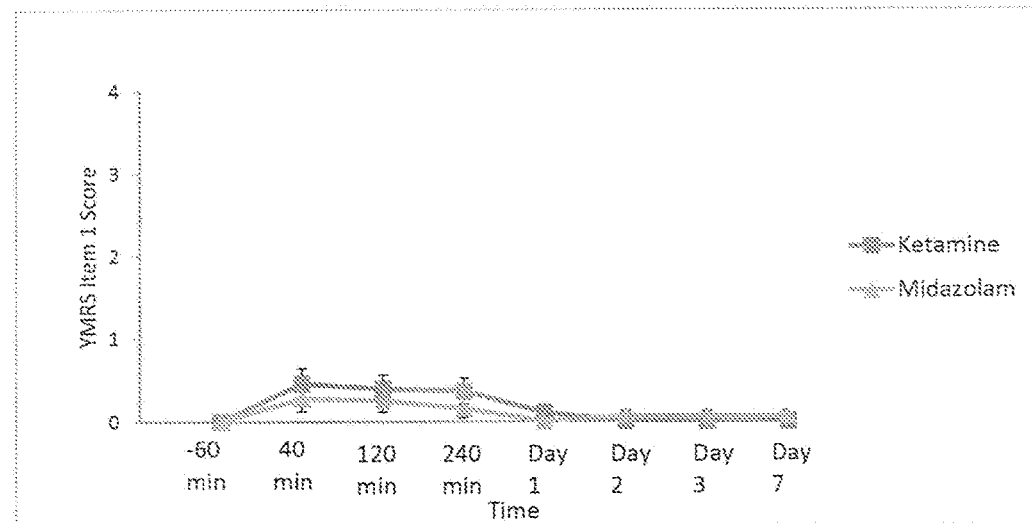

Dissociative symptoms following ketamine were short-lived, peaking at 40 minutes, and had resolved by the next assessment 120 minutes from start of infusion (FIG. 2A). No emergence of significant psychotic or manic symptoms was observed (FIGS. 2B, 2C). One participant dropped out after his second infusion (ketamine), stating that he felt uncomfortable during the infusion due to likely dissociative side effects. Infusion was discontinued after 15 minutes in another patient who received a higher dose of ketamine in error. Three patients required acute treatment with beta-blockers during ketamine infusion because of blood pressure elevation (systolic>180 and/or diastolic>100). On the PRISE, the most frequently reported general side effects of ketamine (vs. midazolam) in the first 24 hours following infusion included blurred vision (6436 vs. 3219%), dry mouth (3621 vs. 2616%), restlessness (4123 vs. 510%), fatigue (3621 vs. 3223%), nausea/vomiting (3621 vs. 53%), poor coordination (2715 vs. 213%), and headache (2313 vs. 1813%).

Discussion

A single dose of ketamine was associated with rapid improvement in core PTSD symptoms in patients with chronic PTSD, compared to a psychoactive placebo control medication, and benefit frequently was maintained beyond 24 hours. Symptoms remained significantly improved in seven ketamine responders compared to one midazolam responder at 2 weeks, as indicated by CAPS score<50. These data provide the first randomized, controlled evidence that NMDA receptor modulation can lead to rapid clinical improvement of core PTSD symptoms in patients with chronic PTSD. Greater improvement in PTSD symptom severity following ketamine compared to midazolam remained significant even after adjusting for baseline and 24-hour depressive symptom severity, thus demonstrating an effect of ketamine on PTSD symptom levels over and above its effects on depressive symptoms. Ketamine was also associated with some improvement in comorbid depressive symptoms, broadening the therapeutic utility of NMDA receptor modulation to the treatment of depressive symptoms in PTSD patients, who frequently have comorbid MDD. Patients also showed improvement in global clinical ratings following ketamine infusion. It was also demonstrated that a single dose of IV ketamine is a safe and well-tolerated intervention in patients with chronic PTSD; ketamine was associated with only transient dissociative symptoms, without significant emergence of psychotic or manic symptoms.

Example 2 provides the first evidence that a single dose of IV ketamine was associated with rapid improvement of core PTSD symptoms and comorbid depressive symptoms in patients with chronic PTSD, and was generally well-tolerated without clinically significant persistent dissociative symptoms.

Example 3: Intranasal Ketamine Treatment of PTSD

The clinical effect of ketamine on PTSD is measured in a blind, double crossover protocol with one or more controls (e.g., midazolam and/or saline). PTSD diagnosis is based on assessment by a study psychiatrist and CAPS (score at least 50 at screening and at each treatment). Patients diagnosed with PTSD receive an intranasal application of either 50 mg ketamine hydrochloride or vehicle placebo. On each of two treatment days, spaced two weeks apart, patients are given one of the two study drugs and, optionally, a group receives only intranasal saline, in random order and under double-blind conditions. Clinical assessments will include the CAPS, TOP-8, HAM-A, MADRS, YMRS-1, BPRS, CADSS, and CGI-S. Self-rated questionnaires will include the IES, QIDS-SR, PRISE, SDS, VAS, PTCI, Sleep questionnaire, Expectancy questionnaire, POMS-Bi, and New Cognitions.

Ketamine is formulated with saline (vehicle) in a nasal spray pump attached to a reservoir bottle Immediately and for 240 minutes following the intranasal application, patients are repeatedly assessed. During and following the administration, TOP-8, HAM-A, MADRS, CADSS, BPRS+/−, IES, QIDS-SR, YMRS-1, PRISE, PTCI, POMS-Bi, New Cognitions, VAS, and CGI-I assessments are conducted. The HVLT is also administered (to assess immediate and delayed recall). Blood samples for assessment of plasma ketamine, norketamine, midazolam, and α-hydroxy-midazolam levels are obtained 30 and 60 minutes after the start of the each infusion. Blood is collected and serum frozen for later testing of ketamine levels. After the acute post-administration period and attainment of sufficient recovery as assessed by the study physician, patients are monitored overnight and then followed up the following morning.

A 24-hour assessment is conducted the morning following each treatment. The following clinician-administered and self-report measures are used: TOP-8, HAM-A, MADRS, IES, PRISE, BPRS, YMRS-1, CADSS, VAS, POMS-Bi, PTCI, New Cognitions, and QIDS-SR.

Follow-Up Visits (5 after Each Treatment):

Patients are assessed at the following time points after the initial treatment: 48 and 72 hours, and 7, 10 and 13 days. The following clinician-administered and self-report measures are used at each visit: TOP-8, HAM-A, BPRS, YMRS-1, CADSS, MADRS, IES, POMS-Bi, PTCI, New Cognitions, VAS, PRISE, and QIDS-SR. At 7 days and 13 days following each treatment the following measures are used: CAPS. In addition, the SDS is used 13 days following each treatment. A study physician rates his/her global impression using the CGI-I. Response is defined as a reduction in IES scores of at least 50% from pre-treatment assessments. Subsequent relapse is defined as the time point at which PTSD symptoms return with sufficient manifestation of core criterion symptoms to meet modified criteria, i.e. CAPS≥50 for ≥2 consecutive study visits or CGI-S of ≥5 on ≥2 consecutive visits. The meetings are focused on psychiatric evaluation. No psychotherapy is conducted.

After Care:

Study participants are offered a period of up to 3 months of free follow-up psychiatric care once they exit the protocol. Follow-up care includes visits with psychiatrists with a frequency determined by their clinical needs and necessary medications. During the three-month follow-up period, study clinicians provide referrals to treating community clinicians and/or referrals to social services agencies.

Data Analyses:

Random effects models are used to model scores over the repeated assessments using the MIXOR or MIXREG software. Prior to random effects modeling, the Shapiro-Wilks test of normality is used to examine the distributions of the outcome variables and visual inspection of histograms and box plots will be performed to identify potential outliers. If variables are not normally distributed or contain outliers, then log transformations are considered. Three separate linear mix models are run to examine the treatment effects of ketamine compared to vehicle control. The first model contains only participants who completed the entire study. A second model includes all participants who enrolled in the study (intent-to-treat). A third model is run on only the first treatment condition day (Treatment Day #1). In this case, the drug effect will be a between-subjects factor instead of a within-subjects factor. To evaluate the proportion of responders and relapsers at each time point, McNemar tests are used beyond 24-hours post-infusion and the results are Bonferroni corrected for the number of points examined Carryover effects from Treatment Day #1 to #2 is examined using a linear mixed model with the same structures as the primary analysis where drug is a within-subjects factor, treatment order is a between subjects factor, and only the baseline measure for each phase is used.

Expected Results:

Intranasal ketamine is expected to induce rapid improvement of core PTSD symptoms and comorbid depressive symptoms in patients with chronic PTSD, and to be generally well-tolerated without clinically significant persistent dissociative symptoms.

Example 4: Randomized Controlled Trial of Repeated-Dosing Intranasal Ketamine Administration for Treatment of PTSD Overview:

The predominant theory of PTSD postulates that PTSD patients are poor at extinguishing acquired fear. The most common treatment, consequently, is exposure therapy in which patients are gradually and repeatedly exposed to fear triggering cues in a safe environment until their fear responses dissipate. This strategy to control maladaptive fear is often short-lived because the suppressed fear typically comes back with the passage of time, a change of place, or after stressful life exposure. These events are inevitable in an ever-changing environment, and the patients constantly confront challenges to their capability to keep fear under siege. It has been shown in animals that ketamine induces a late phase of neural plasticity (24 hours post-administration). This suggests that by timing ketamine administration such that its subsequent effects would coincide with learning might provide a novel way to enhance exposure therapy or extinction training pharmacologically.

The efficacy of repeated intranasal administration of ketamine in providing (1) rapid relief of and (2) sustained improvement in core PTSD symptoms and co-morbid depressive symptoms in patients with chronic PTSD is tested in a parallel-arm, double-blind, randomized controlled clinical trial. The effects of ketamine are compared with those of repeated intranasal administration of the benzodiazepine anesthetic midazolam, which mimics some of the acute subjective effects of ketamine but is expected to have lesser or less sustained anxiolytic effect, and no sustained antidepressant effect, and/or with those of repeated intranasal saline administration. Patients with chronic PTSD are randomized to receive repeated intranasal administrations of either ketamine or midazolam, administered 3 times a week over the course of 4 consecutive weeks. Another control group can include patients randomized to receive intranasal saline.

Expected Outcomes:

1: Repeated intranasal administration of ketamine is expected to be effective in (1) rapidly reducing core PTSD symptoms and (2) maintaining improvement in core PTSD symptoms, measured over time, compared to repeated intranasal administration of midazolam or repeated intranasal saline administration.

2: Repeated intranasal administration of ketamine is expected to be effective in (1) rapidly reducing co-morbid depressive symptoms and (2) maintaining improvement in co-morbid depressive symptoms, measured over time, compared to repeated intranasal administration of midazolam or repeated intranasal saline administration.

3: Ketamine administered via the intranasal route is expected to be well tolerated, with limited side effects including short-lived dissociative effects.

4. Repeated intranasal administration of ketamine is expected to enhance extinction training and prevent the return of learned fear responses.

Study Protocol:

Inclusion and Exclusion Criteria:

Inclusion

Men or women, 18-65 years of age;

Participants must have a level of understanding sufficient to agree to all tests and examinations required by the protocol and must sign a written informed consent document;

Participants must fulfill DSM-5 criteria for current civilian or combat-related PTSD, based on clinical assessment by a study psychiatrist and on the CAPS (score must be at least 50 at screening and prior to the first intranasal administration—this is done to ensure at least moderate severity and to safeguard against high placebo response rates);

Women must be using a medically accepted reliable means of contraception (if using an oral contraceptive medication, they must also be using a barrier contraceptive) or not be of childbearing potential (i.e., surgically sterile, postmenopausal for at least one year);

Women of childbearing potential must have a negative pregnancy test at screening and prior to each intranasal administration;

Participants must be able to identify a family member, physician, or friend (i.e. someone who knows them well) who will participate in a Treatment Contract (and, e.g., contact the study physician on their behalf in case manic symptoms or suicidal thoughts develop).

Patients with civilian as well as combat-related PTSD are included. It is expected that around 50% of the sample will be patients with combat-related PTSD (recruited through the James J. Peters VA Medical Center). This will allow performance of exploratory analyses on the efficacy of ketamine in combat-related vs. civilian PTSD. As in the completed study of IV ketamine vs. midazolam or saline for PTSD, patients with co-morbid MDD (except those with bipolar or psychotic depression) are not excluded, because it is believed that this will affect the generalizability of the findings. Almost 50% of patients with PTSD have co-morbid diagnosis. Allowing patients with histories of co-morbid MDD to participate broadens the inclusion criteria to more closely approximate PTSD patients seen in real-world settings. Also, it allows the investigation of the antidepressant effect of ketamine in PTSD patients with co-morbid MDD. In general, inclusion/exclusion criteria are intended to protect patient welfare where, for example, administration of ketamine in the context of standardized research would be inadvisable or unsafe (e.g., because of pregnancy, history of allergy or other intolerance to study drug, or active suicidality). An additional purpose is to limit variability due to demographic and other factors, and to decrease psychiatric co-morbidities that may affect the clinical phenomenology or treatment response and thus obscure findings (e.g. primary diagnosis of bipolar disorder or schizophrenia, co-morbid substance use disorder).

Exclusion

Women who plan to become pregnant, are pregnant or are breast-feeding (because the medical risk of using ketamine during pregnancy and breast-feeding is unknown);

Serious, unstable medical illnesses such as hepatic, renal, gastroenterologic, respiratory, cardiovascular, endocrinologic, neurologic, immunologic, or hematologic disease, including gastro-esophageal reflux disease, obstructive sleep apnea, history of difficulty with airway management during previous anesthetics, ischemic heart disease and uncontrolled hypertension, and history of severe head injury;

Clinically significant abnormal findings of laboratory parameters, physical examination, or ECG;

Patients with uncorrected hypothyroidism or hyperthyroidism;

Hormonal treatment (e.g., estrogen) started in the 3 months prior to the first intranasal administration day;

Use of evidence-based individual psychotherapy (such as prolonged exposure) and other non-pharmacological treatments during the study;

Histories of autism, mental retardation, pervasive developmental disorders, or Tourette's syndrome;

History of one or more seizures without a clear and resolved etiology;

History of (hypo)mania;

Past or current presence of psychotic symptoms, or diagnosis of a lifetime psychotic disorder including schizophrenia or schizoaffective disorder;

Drug or alcohol abuse or dependence within the preceding 3 months; a rather narrow time period was chosen, however, in order to allow participation by individuals with a history of substance abuse or dependence problems that could be secondary to their PTSD, and to more closely approximate patients seen in real-world settings;

Previous recreational use of ketamine or PCP;

Current diagnosis of bulimia nervosa or anorexia nervosa;

Diagnosis of schizotypal or antisocial personality disorder (since these are known to reduce the possibility of study completion); other Axis II diagnoses will be allowed;

Patients judged clinically to be at serious and imminent suicidal or homicidal risk.

A blood pressure of one reading over 160/90 or two separate readings over 140/90 at screen or baseline visits;

Patients who report current treatment with a benzodiazepine, an opioid medication, a mood stabilizer (such as valproic acid or lithium), or prazosin within 2 weeks prior to randomization; patients taking stable doses of antidepressant medication for 3 months prior to randomization will be allowed.

Number of Subjects:

A sample size of N=40 (total number of participants expected to complete study procedures) is established based on considerations of estimated effect size in parallel-arm, repeated dose, active control design, and feasibility of subject recruitment (see Data Analysis Plan, below).

Parallel Arm Design:

Given that ketamine or midazolam is administered 3 times per week over 4 weeks, the following modified parallel-arm design is employed: during study conduct, partially unblinded sequential analyses are conducted. Other study investigators remain fully blinded. While, at the beginning of the study, participants are randomized to ketamine or midazolam with a 50/50 ratio, if results of sequential analyses indicate that response to one treatment is higher than to the other treatment, this ratio is shifted to 60/40 in favor of the treatment with better results. An additional group of patients is optionally randomized to receive intranasal saline for comparison.

Study Endpoints:

The primary outcomes are change in PTSD symptom severity measured 24 hours after the first drug administration with the IES-R, and at 1, 2, 3 and 4 weeks after the first drug administration, measured with the CAPS for DSM-5.

Secondary Outcomes:

PTSD symptom severity is measured at each drug administration day with the IES-R. Depressive symptom severity is measured with the QIDS-SR and the MADRS 24 hours after the first drug administration, with the QIDS-SR at each drug administration day, and the MADRS at 1, 2, 3, and 4 weeks after the first drug administration day.

Treatment-emergent side effects are measured with the PRISE at each study session (drug administration day). Functional impairment will be assessed with the SDS. Additionally, resilience, psychological growth and life satisfaction will be measured with the CD-RISC, the Purpose in Life Scale, the abbreviated MOS Social Support Survey, the PTGI, and the Q-LES-Q. Fear conditioning, extinction and reinstatement are assessed by measuring the skin conductance response ("SCR"). See, Schiller, D., & Delgado, M. R. (2010). Overlapping neural systems mediating extinction, reversal and regulation of fear. Trends in cognitive sciences, 14(6), 268-276.

Screening and Washout Period:

After receiving complete disclosure about the research and opportunity to fully review the consent form, potential participants are given the opportunity to ask questions. If they choose to take part in the study, then they are asked to sign the written informed consent form. Medical and psychiatric history and response to previous treatments are obtained by a study investigator, and the diagnosis of PTSD is made using the CAPS for DSM-5 (described above, see, Weathers, F. W., et al (2013). The Clinician-Administered PTSD Scale for DSM-5 (CAPS-5). Interview available from the National Center for PTSD at ptsd.va.gov on the WorldWideWeb). The presence of any co-morbid diagnoses is ascertained with the SCID-P for DMS-5. The SCID-P for DSM-5 is called SCID for DSM-5, Patient version. This is the next edition of SCID modified to incorporate the new DSM-5 criteria.

At screening, participants are also administered a battery of cognitive tests to quantify cognitive function at baseline, including tests of processing speed, attention, working memory, learning, and executive function (reasoning and problem solving).

All patients have a physical examination and specific laboratory tests. These tests include: a physical examination, electrocardiogram (ECG), supine and standing vital signs, complete blood cell counts, hepatitis B and C screen, electrolytes, thyroid function tests, fasting blood sugars and chemistries, liver function tests, urinalysis and toxicology screening. A pregnancy test is performed in premenopausal women. After Screening (which generally takes 2-3 visits), participants are expected to meet all inclusion and exclusion criteria listed above.

Patients who are taking allowed psychotropic medications at screening (e.g., antidepressant medications) at stable doses for 3 months prior to enrolling in the study (without changes, including adding or stopping any such medication) are considered for participation and are allowed to continue taking these medications. It is asked that they do not make any changes in dosage of these medications, or start or stop any medication for emotional or psychiatric symptoms, for the duration of the study. If it becomes necessary to change, adjust or stop their psychiatric medication while in this study, this will end the participant's involvement in the study.

If at screening patients are taking psychotropic medication that is not allowed in the study (e.g., a benzodiazepine), they must be drug-free for a minimum of 2 weeks prior to Visit 1 (the first intranasal ketamine or midazolam or saline administration). Patients who are benefiting from medications that are not permitted in the study will not be tapered off such medications and are excluded from the study. Patients who experience withdrawal symptoms from the medication taper may have this drug-free period extended. The monitoring of the tapering or "washout" of psychotropic medications is conducted by the patient's prescribing physician, with consultation from the study physician investigators. Study physician investigators will actively participate in this process only if a patient no longer has an active treatment relationship with her/his prescribing physician. Following medical and psychiatric screening, and if required a washout period of 2 weeks from medications that are not permitted in the study (exclusion criteria), eligible patients are randomized to ketamine or midazolam or saline treatment. An additional group of patients receive intranasal saline as a comparison group. Patients who continue to meet symptomatic threshold of severity within 24 hours prior to the first administration (CAPS≥50) will receive the first intranasal administration of ketamine (5 intranasal sprays, 15 mg/spray, every 5 minutes over 20 minutes, total up to 75 mg) or intranasal midazolam (5 intranasal sprays, 0.75 mg/spray, every 5 minutes over 20 minutes, total up to 3.75 mg) or saline (5 intranasal sprays).

After the first administration of intranasal ketamine or midazolam or saline (on a Monday), treatment consists of 11 additional intranasal ketamine or midazolam or saline administrations conducted on Wednesday, Friday (first week); and on Monday, Wednesday, and Friday (of weeks 2, 3, and 4), each preceded and followed by clinical assessments. Any participant who experiences intolerable side effects during the $1^{st}$ intranasal administration, including hemodynamic (e.g., significant increase in blood pressure) or other side effects (e.g., significant dissociation or sedation), is administered the next possible lower dose, consisting of up to 4 intranasal sprays (up to 60 mg of ketamine or up to 3 mg of midazolam) on the $2^{nd}$ administration day. If, on this $2^{nd}$ administration day, the participant again experiences intolerable side effects, he/she is administered the next possible lower dose, consisting of up to 3 intranasal sprays (up to 45 mg of ketamine or up to 2.25 mg of midazolam) on the $3^{rd}$ administration day. If on this $3^{rd}$ administration day, the participant again experiences intolerable side effects on this lower dose, he/she is exited from the study. Participants who tolerate study drug administration without significant side effects continue to receive the same maximum total dose that they were able to tolerate, ranging from 3 to 5 intranasal sprays per administration day.

The first primary outcome measure is the IES-R score at 24 hours after the first IN administration. The second primary outcome measure is the CAPS score at the end of weeks 1, 2, 3 and 4. Secondary outcome measures include the IES-R, QIDS-SR, CGI-S and CGI-I, administered at visits 1b (24 hours after the first intranasal administration), 2, 3, 4, 5, 6, 7, 8, 9, 10, 11, 12 and 13 (end of week 4), as well as the MADRS, administered at the end of weeks 1, 2, 3 and 4. Additionally, the MADRS will also be administered at 24 hours after the first intranasal administration.

Additional secondary outcome measures include the CD-RISC, the Purpose in Life Scale, the abbreviated MOS Social Support Survey, the PTGI and the Q-LES-Q, administered at the end of weeks 2 and 4 (in addition to baseline).

Visit 1a: First IN Ketamine Administration

Patients receive a baseline blood draw at 8:00 a.m. after an overnight fast for solid food and non-clear liquids. Blood is processed and stored for future measurement of hormone, neurotrophic and inflammatory biomarkers, as well as for genetic, epigenetic and gene expression studies.

Subsequently, prior to the first ketamine or midazolam or saline administration, subjects undergo fear conditioning, in which they learn to associate a stimulus with a mild electric shock. Specifically, a negative or neutral stimulus is presented to the subject on a computer screen: visually, tonally, or both. The stimulus, if visual, is a colored shape, simple figure, emotional or neutral word, emotional or neutral face, or a neutral photograph. If auditory, the stimulus is a beep or tone. Some stimuli, conditioned stimuli, are sometimes followed by an aversive outcome (e.g., non-painful shock to the wrist or ankle or negative image presentation). Other stimuli are never followed by an outcome and are used for comparison. SCR is measured throughout.

Patients have all procedures performed in a private, quiet room. Initial assessments are performed by the same continuous rater (CR-1) who performs the initial Screening assessment. The CAPS is administered within 24 hours prior to the first administration and must remain ≥50 in order for the participant to be eligible.

A urine toxicology and, for women, pregnancy screen is performed. In the mornings of treatment days, initial assessments include the IES-R, QIDS-SR, HAM-A, BPRS, CADSS, SDS, CGI, VAS, and POMS. At visit 1a (and selected visits listed below), assessments additionally include the TOP-8, MADRS and CAPS.

An indwelling catheter is placed in the antecubital vein of the nondominant arm, and pulse, blood pressure, digital pulse-oximetry, and ECG monitoring is instituted. All physiologic monitoring data is recorded on a standard anesthesia record beginning five minutes prior to ketamine administration. At 9:00 am each patient receives an intranasal administration of up to 75 mg of ketamine or up to 3.75 mg of midazolam or saline over a period of 20 minutes. Ketamine or midazolam is dissolved in a total volume of 1.5 ml, to be given in up to 5 intranasal administrations of 0.3 ml each, every 5 minutes for a total of 20 minutes, in a nasal spray pump attached to a reservoir bottle Immediately and for 240 minutes following the intranasal application, patients are repeatedly assessed by means of clinician-administered and self-report rating scales, including scales to assess side effects. Mood and symptom ratings during and following the administration are conducted by a separate rater (CR-2). Inter-rater reliability is established for all outcome measures prior to study. Blood is collected and serum frozen for later testing of ketamine and midazolam levels.

Visit 1b (24 Hours Post First Ketamine Administration)

Patients receive a blood draw at 8:00 am. Blood is processed and stored for future measurement of hormone, neurotrophic and inflammatory biomarkers, as well as for epigenetic and gene expression studies. Between 9 and 10 a.m. the next morning, participants undergo extinction training, where they are repeatedly exposed to the same stimuli but without the aversive outcomes (e.g., no electric shocks). SCR is measured throughout.

The patients are additionally assessed by the same rater who conducted the ratings prior to intranasal administration (CR-1), and receive all assessment scales administered at Visit 1a.

Visit 2 (48 Hours Post First Ketamine or Midazolam Administration)

On Visit 2, prior to the second ketamine or midazolam or saline administration, participants undergo reinstatement (exposure to few electric shocks without the visual stimuli) to reinstate the learning that was extinguished on the previous stage (on visit 1a), after which they are presented with the stimuli again (with no outcome) to measure if the memory was recovered. SCR is measured throughout.

Patients are then assessed by the IES-R, QIDS-SR, HAM-A, BPRS, CADSS, SDS, CGI, VAS, and POMS.

Participants in this study receive ketamine or midazolam or saline under blinded conditions. Procedures to be followed before, during, and after each administration are identical to those used during Visit 1a. Clinical ratings prior to each intranasal administration are obtained by the same rater who evaluated prior to the first intranasal administration (CR-1). Ratings conducted on intranasal administration days during and after intranasal ketamine, midazolam, or saline administration are administered by the same rater who administers ratings on all study days after intranasal ketamine or midazolam or saline administration (CR-2). It is expected that no significant psychotomimetic side effects will occur, such that patients can be discharged at 240 minutes post-intranasal administration.

Visits 3-12

Since Visits 1a and 2 take place on a Monday and Wednesday, respectively, Visits 3-12 take place on the following Friday; Monday, Wednesday, Friday; Monday, Wednesday, and Friday; and Monday, Wednesday, and Friday. In the event of a Monday holiday, intranasal administration of ketamine, midazolam, or saline take place one day later.

Procedures to be followed before, during, and after each administration are identical to those used during Visit 1a. Clinical ratings continue to be obtained by the same raters who evaluated patients prior to intranasal administration (CR-1) and following intranasal administration (CR-2), respectively. If, at any point during treatment patients do exhibit significant psychotomimetic side effects during intranasal administration, resulting in need for additional monitoring beyond 5:00 pm on the day of administration, they are exited from the study following additional observation.

In addition to the rating instruments and scales mentioned above, rater CR1 will administer the CAPS once a week (prior to the first intranasal administration, and 1, 2, 3 and 4 weeks after the first intranasal administration, usually on Mondays unless there is a Monday holiday, in which case it is administered the following day).

At Visits 4, 7 and 10, the list of assessments is the same as that on Visit 1a.

At Visit 7 (2 weeks after first drug administration), patients are again administered the battery of cognitive tests to assess any potential changes in cognitive function compared to baseline. Patients also receive a 2-week biomarker blood draw (2-3 tablespoons of blood) at this time point.

Visit 13 (after all Administrations are Completed)

Laboratory testing is repeated three days after the conclusion of ketamine or midazolam or saline treatment. Patients also receive a final 4-week biomarker blood draw (2-3 tablespoons of blood) at this time point. Blood is processed and stored for future measurement of hormone, neurotrophic and inflammatory biomarkers, as well as for epigenetic and gene expression studies.

Patients are assessed with the TOP-8, CAPS and the MADRS by the same rater who performed these assessments at Visit 1a prior to the first intranasal administration (CR-1). Patients are also be assessed by a study physician with CGI-I and CGI-S scales, and are asked to complete the IES-R, QIDS-SR, the POMS and the VAS.

During this visit (4 weeks after first drug or saline administration), patients are again administered the battery of cognitive tests, to assess any changes in cognitive function compared to baseline.

Visits 14-18 (Weekly Follow-Ups)

Patients are assessed with the CAPS and MADRS by the same rater who performed these assessments at Visit 1a prior to the first intranasal administration, and with CGI-I and CGI-S scales by a study physician. Patients also complete the IES-R, QIDS-SR, the POMS and the VAS.

Visits 19-22 (Monthly Follow-Ups)

Patients are assessed with the CAPS and MADRS by the same rater who performed the assessments on the morning of Visit 1a (CR-1), and with CGI-I and CGI-S scales by a study physician. Patients also complete the IES-R, QIDS-SR, the POMS, and VAS.

Data Analysis Plan:

Partially unblinded sequential data analyses ("drug A/drug B") are conducted each time 5 additional participants complete study procedures by one investigator. All other study investigators remain fully blinded. Based on findings from this data analysis, if response to one drug is superior to response to the other drug, the randomization ratio will switch from 50%-50% to 60%-40% favoring the drug with superior effect.

Co-primary outcomes are used to evaluate the short-term effect of the initial intranasal administration of ketamine and the longer-term effects of repeated intranasal administrations of ketamine compared to an active control (midazolam) or saline.

A paired two-sample t-test is used to compare mean IES-R scores in the two treatment groups at 24 hours after the first study drug administration. Based on data from a recent study of a single infusion, a decrease of 30 (sd=10) from baseline of 45 is expected in the ketamine arm, and a decrease of 25 (sd=10) is expected in the midazolam arm. A paired t-test is chosen in order to determine whether IES-R scores improved compared to baseline and whether the change was different between treatment groups. A sample size of 40 will provide 89% power assuming a Type I error rate of 0.05. Scores can also be compared to a saline-treated group.

To assess longer-term effects of repeated study drug administrations, mean CAPS scores at 7 days after the initial administration are compared using a paired two-sample t-test. If the difference between ketamine and midazolam is statistically significant at 7 days, mean CAPS scores at baseline and at 28 days after the initial administration are compared between groups using a paired two-sample t-test. This sequential testing, or gatekeeping, strategy is used to preserve Type I error and increase power. In the single infusion study, a decrease of 27 (sd=20) in CAPS score at 7 days was seen in the ketamine arm compared to a decrease of 13 (sd=18) in the midazolam arm. Assuming a sample size of 40, these conservative estimates provide 96% power assuming a Type I error rate of 0.025 (using the Bonferroni adjustment to hold the family-wise error rate at 0.05).

Psychophysiological Analysis:

The psychophysiological index of fear is the differential SCR (i.e., the difference between reinforced versus non-reinforced stimuli). The SCR level is assessed for each trial as the peak-to-peak amplitude difference of the largest deflection in the 0.5-4.5 seconds (s) latency window from stimulus onset. The minimal response criterion is 0.02 microsiemens ($\mu$S). The raw SCR scores are square root transformed to reduce distribution skewness, and scaled according to each subject's mean square-root-transformed unconditioned stimulus (US) response. To assess the development of learning over time, each phase is divided into an early (first half) and a late (second half) stage. The mean differential SCR for each stage is calculated within subjects. To assess expectations to the shocks, rather than responses to the shocks themselves, trials co-terminating with the shock are not included in the analysis, but are assessed separately to verify that responses to the intensity of the shock do not correlate with symptomatology scores.

The present disclosure is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method of treating post-traumatic stress disorder (PTSD) in a patient determined to be suffering from PTSD, comprising conducting a psychiatric evaluation of a patient to determine if the patient is afflicted with PTSD, and intranasally administering to a patient determined to be suffering from PTSD multiple sub-analgesic therapeutic doses of ketamine of between about 0.01 to about 3.0 mg of ketamine per kilogram of body weight of the patient (mg/kg).

2. The method of claim 1, wherein a first dose is between about 0.01 to about 2.0 mg of ketamine per kilogram of body weight of the patient (mg/kg).

3. The method of claim 2, wherein the first dose is between about 0.05 to about 0.5 mg/kg of ketamine.

4. The method of claim 2, wherein the first dose is less than about 0.5 mg/kg, less that about 0.4 mg/kg or less than about 0.3 mg/kg of ketamine.

5. The method of claim 1, which comprises administering the doses of ketamine at weekly intervals.

6. The method of claim 5, wherein the patient is treated with one dose of ketamine per week for a period of two or more weeks.

7. The method of claim 1, further comprising administering a second agent to treat the PTSD.

8. The method of claim 7, wherein the second agent is an anti-depressant.

9. The method of claim 7, wherein the second agent is selected from the group consisting of paroxetine, sertraline, lithium, riluzole, prazosin, lamotrigine and ifenprodil.

10. The method of claim 7, wherein the second agent is used as adjunctive therapy to ketamine treatment.

11. The method of claim 7, wherein the treatment comprises a phase wherein treatment with the second agent takes place after treatment with ketamine has ceased.

12. The method of claim 1, wherein the ketamine is administered in a composition comprising a pharmaceutically acceptable carrier, excipient or diluent.

13. The method of claim 1, wherein the ketamine is esketamine.

14. The method of claim 1, wherein the total dose of ketamine is about 1.1 mg/kg.

15. The method of claim 1 which comprises determining if the patient determined to be suffering from PTSD has responded to the first dose of ketamine, and administering to the patient a second dose of ketamine if the patient has responded to the first dose of ketamine, wherein the second dose is lower than the first dose.

16. The method of claim 1 which comprises determining if the patient determined to be suffering from PTSD has responded to the first dose of ketamine and administering to the patient a second dose of ketamine, wherein the second dose is higher than the first dose.

17. A method of treating post-traumatic stress disorder (PTSD) in a patient determined to be suffering from PTSD, comprising administering to a human individual suffering from PTSD a first therapeutically effective amount of ketamine between about 0.01 to about 3.0 mg of ketamine per kilogram of body weight of the patient (mg/kg) and then administering to the individual a second therapeutically effective amount of ketamine, wherein the second therapeutically effective amount of ketamine is lower or higher than the first therapeutically effective amount of ketamine.

18. The method of claim 17 wherein the individual suffering from PTSD additionally suffers from at least one comorbid depressive condition.

19. The method of claim 18 wherein the second therapeutically effective amount of ketamine is lower than the first therapeutically effective amount of ketamine.

20. The method of claim 17 wherein the ketamine is esketamine.

21. The method of claim 17 wherein the first therapeutically effective amount of ketamine is between about 0.01 to about 2.0 mg of ketamine per kilogram of body weight of the patient (mg/kg).

22. The method of claim 17 which further comprises evaluating the patient after administering the first dose of ketamine to determine if the patient's PTSD symptoms have been alleviated.

23. The method of claim 22 wherein the evaluating step comprises conducting at least one of the SCID-P, CAPS, CAPS-5 or TOP-8 structured interviews with the patient and scoring the test results.

24. A method of treating post-traumatic stress disorder (PTSD) in a patient determined to be suffering from PTSD, comprising administering to a human individual suffering from PTSD a first therapeutically effective amount of ketamine between about 0.01 to about 3.0 mg of ketamine per kilogram of body weight of the patient (mg/kg), measuring the efficacy of the treatment in relieving the symptoms of PTSD after the administering step and, provided that one or more symptoms of PTSD or a comorbid depressive condition are alleviated, administering to the individual a second therapeutically effective amount of ketamine, wherein the second therapeutically effective amount of ketamine is lower or higher than the first therapeutically effective amount of ketamine.

25. The method of claim 24 wherein the second therapeutically effective amount of ketamine is lower than the first therapeutically effective amount of ketamine.

26. The method of claim 24 wherein the second therapeutically effective amount of ketamine is higher than the first therapeutically effective amount of ketamine.

27. The method of claim 24 wherein the core symptoms of PTSD are relieved after administration of the first therapeutically effective amount of ketamine.

28. A method of treating post-traumatic stress disorder (PTSD) in a patient determined to be suffering from acute symptoms of PTSD, comprising administering to a human individual suffering from acute symptoms of PTSD a first therapeutically effective amount of ketamine to treat said acute symptoms and thereafter administering to the individual a second lower amount of ketamine to treat chronic symptoms of PTSD.

29. The method of claim 28 which comprises titrating the amount of ketamine to reach the second lower amount of ketamine.

30. The method of claim 24 wherein the measuring step comprises conducting an interview with the human individual using at least one of the SCID-P, CAPS, CAPS-5 or TOP-8 structured interviews and scoring the test results.

31. The method of claim 24 wherein the first therapeutically effective amount is between about 0.01 to about 2.0 mg of ketamine per kilogram of body weight of the patient (mg/kg).

32. A method of treating post-traumatic stress disorder (PTSD) in a patient determined to be suffering from PTSD, comprising administering to a human individual suffering from PTSD a first therapeutically effective amount of ketamine between about 0.01 to about 3.0 mg of ketamine per kilogram of body weight of the patient (mg/kg), measuring the efficacy of the treatment in relieving the symptoms of PTSD after the administering step and, provided that one or more symptoms of PTSD or a comorbid depressive condition are alleviated, administering to the individual a second therapeutically effective amount of ketamine.

33. The method of claim 1 wherein the intranasal administration comprises administering the ketamine to the olfactory epithelium at the roof of the nasal cavity.

34. The method of claim 1 wherein the administering step bypasses the blood brain barrier.

* * * * *